(12) United States Patent
Cullis et al.

(10) Patent No.: US 7,811,602 B2
(45) Date of Patent: Oct. 12, 2010

(54) LIPOSOMAL FORMULATIONS COMPRISING DIHYDROSPHINGOMYELIN AND METHODS OF USE THEREOF

(75) Inventors: Pieter R Cullis, Vancouver (CA); Thomas D Madden, Vancouver (CA); Michael J Hope, Vancouver (CA); Steven M Ansell, Vancouver (CA); Barbara L S Mui, Vancouver (CA); Sean C Semple, Vancouver (CA); Norbert Maurer, Vancouver (CA)

(73) Assignee: Tekmira Pharmaceuticals Corporation, Burnaby (CA)

( * ) Notice: Subject to any disclaimer, the term of this patent is extended or adjusted under 35 U.S.C. 154(b) by 1249 days.

(21) Appl. No.: 11/131,436

(22) Filed: May 16, 2005

(65) Prior Publication Data

US 2006/0008909 A1 Jan. 12, 2006

Related U.S. Application Data

(60) Provisional application No. 60/631,997, filed on Nov. 30, 2004, provisional application No. 60/571,712, filed on May 17, 2004.

(51) Int. Cl.
*A61K 9/127* (2006.01)

(52) U.S. Cl. .................................................. 424/450

(58) Field of Classification Search .................. 424/450
See application file for complete search history.

(56) References Cited

U.S. PATENT DOCUMENTS

| | | | |
|---|---|---|---|
| 4,186,183 A | 1/1980 | Steck et al. | 424/38 |
| 4,217,344 A | 8/1980 | Vanlerberghe et al. | 424/60 |
| 4,235,871 A | 11/1980 | Papahadjopoulos et al. | 424/19 |
| 4,261,975 A | 4/1981 | Fullerton et al. | 424/89 |
| 4,485,054 A | 11/1984 | Mezei et al. | 264/4.6 |
| 4,501,728 A | 2/1985 | Geho et al. | 424/38 |
| 4,603,044 A | 7/1986 | Geho et al. | 424/9 |
| 4,737,323 A | 4/1988 | Martin et al. | 264/4.3 |
| 4,774,085 A | 9/1988 | Fidler | 424/85.5 |
| 4,837,028 A | 6/1989 | Allen | 424/450 |
| 4,857,319 A | 8/1989 | Crowe et al. | 424/94.1 |
| 4,880,635 A | 11/1989 | Janoff et al. | 424/450 |
| 4,885,172 A | 12/1989 | Bally et al. | 424/417 |
| 4,942,184 A | 7/1990 | Haugwitz et al. | 514/449 |

(Continued)

FOREIGN PATENT DOCUMENTS

WO    WO 91/17424    11/1991

(Continued)

OTHER PUBLICATIONS

Abra, R., et al., "The Next Generation of Liposome Delivery Systems: Recent Experience with Tumor-targeted, Sterically-stabilized Immunoliposomes and Active-loading Gradients," *J Liposome Res.*, 12(1-2):1-3, Feb.-May 2002.

(Continued)

*Primary Examiner*—Gollamudi S Kishore
(74) *Attorney, Agent, or Firm*—Seed IP Law Group PLLC

(57) ABSTRACT

The present invention includes novel liposomes comprising dihydrosphingomyelin. The invention also includes compositions comprising these liposomes and a therapeutic agent, in addition to methods and kits for delivering a therapeutic agent or treating a disease, e.g., a cancer, using these compositions.

18 Claims, 14 Drawing Sheets

U.S. PATENT DOCUMENTS

| | | | | |
|---|---|---|---|---|
| 4,946,787 | A | 8/1990 | Eppstein et al. | 435/240.2 |
| 4,957,773 | A | 9/1990 | Spencer et al. | 427/39 |
| 5,013,556 | A | 5/1991 | Woodle et al. | 424/450 |
| 5,059,421 | A | 10/1991 | Loughrey et al. | 424/417 |
| 5,077,056 | A | 12/1991 | Bally et al. | 424/450 |
| 5,171,578 | A | 12/1992 | Bally et al. | 424/450 |
| 5,376,380 | A | 12/1994 | Kikuchi et al. | 424/450 |
| 5,534,499 | A | 7/1996 | Ansell | 514/25 |
| 5,543,152 | A * | 8/1996 | Webb et al. | 424/450 |
| 5,578,320 | A | 11/1996 | Janoff et al. | 424/450 |
| 5,736,155 | A | 4/1998 | Bally et al. | 424/450 |
| 5,741,516 | A | 4/1998 | Webb et al. | 424/450 |
| 5,814,335 | A | 9/1998 | Webb et al. | 424/450 |
| 5,817,334 | A | 10/1998 | Schmidt et al. | 424/450 |
| 5,820,873 | A | 10/1998 | Choi et al. | 424/283.1 |
| 5,837,279 | A | 11/1998 | Janoff et al. | 424/450 |
| 5,837,282 | A * | 11/1998 | Fenske et al. | 424/450 |
| 5,858,398 | A * | 1/1999 | Cho | 424/450 |
| 5,885,613 | A | 3/1999 | Holland et al. | 424/450 |
| 5,922,350 | A | 7/1999 | Janoff et al. | 424/450 |
| 5,976,567 | A | 11/1999 | Wheeler et al. | 424/450 |
| 5,981,564 | A | 11/1999 | Pagé et al. | 514/400 |
| 6,320,017 | B1 | 11/2001 | Ansell | 528/310 |
| 6,355,267 | B1 | 3/2002 | Collins | 424/450 |
| 6,380,405 | B1 | 4/2002 | Ekwuribe et al. | 549/510 |
| 6,475,517 | B1 | 11/2002 | Tagawa et al. | 424/450 |
| 6,610,835 | B1 | 8/2003 | Liotta et al. | 536/4.1 |
| 2002/0041897 | A1 | 4/2002 | Dang | 424/486 |
| 2002/0110586 | A1* | 8/2002 | Madden et al. | 424/450 |
| 2002/0119990 | A1 | 8/2002 | Madden et al. | 514/283 |
| 2004/0071768 | A1 | 4/2004 | Sarris et al. | 424/450 |
| 2004/0228909 | A1 | 11/2004 | Sarris et al. | 424/450 |

FOREIGN PATENT DOCUMENTS

| | | |
|---|---|---|
| WO | WO 95/08986 | 4/1995 |
| WO | WO 02/072010 A2 | 9/2002 |

OTHER PUBLICATIONS

Allen, T., et al., "Large Unilamellar Liposomes with Low Uptake into the Reticuloendothelial System," *FEBS Lett.*, 223(1):42-6, Oct. 19, 1987.

Allen, T., et al., "Liposomes Containing Synthetic Lipid Derivatives of Poly(ethylene glycol) Show Prolonged Circulation Half-lives in Vivo," *Biochim Biophys Acta.*, 1066(1):29-36, Jul. 1, 1991.

Allen, T., et al., "A New Strategy for Attachment of Antibodies to Sterically Stabilized Liposomes Resulting in Efficient Targeting to Cancer Cells," *Biochim Biophys Acta.*, 1237(2):99-108, Jul. 26, 1995.

Allen, T., et al., *Liposomes*, Janoff, A.S. (ed.), Marcel Dekker Inc., New York, 1999, Ch. 3, "Liposome Pharmacokinetics—Classical, Sterically Stabilized, Cationic Liposomes and Immunoliposomes," pp. 63-87.

Bangham, A.., et al., "Ultrastructure of Membranes: Biomolecular Organization," *Br Med Bull.*, 24(2):124-6, May 1968.

Bangham, A., "Membrane Models with Phospholipids," *Prog Biophys Mol Biol.*, 18:29-95, 1968.

Barenholz, Y., et al., "A Calorimetric Study of the Thermotropic Behavior of Aqueous Dispersions of Natural and Synthetic Sphingomyelins," *Biochemistry.*, 15(11):2441-7, Jun. 1, 1976.

Barenholz, Y., et al., In *Physiology of Membrane Fluidity*, vol. 1, Shinitsky, M. (ed.), CRC Press, Boaca Raton, FL, Ch. 5, "Sphingomyelin-Lecithin Balance in Membranes: Compositions, Structure, and Function Relationships," pp. 131-174.

Bloomfield, V., "Quasi-Elastic Light Scattering Applications in Biochemistry and Biology," *Ann. Rev. Biophys. Bioeng.* 10:421-450, 1981.

Blume, G., et al., "Specific Targeting with Poly(ethylene glycol)-modified Liposomes: Coupling of Homing Devices to the Ends of the Polymeric Chains Combines Effective Target Binding with Long Circulation times," *Biochim Biophys Acta.*, 1149(1):180-4, Jun. 18, 1993.

Boman, L., et al., "Liposomal Vincristine which Exhibits Increased Drug Retention and Increased Circulation Longevity Cures Mice Bearing P388 Tumors," *Cancer Res.*, 54(11):2830-3, Jun. 1, 1994.

Byrdwell, W., et al., "Liquid Chromatography/mass-spectrometric Characterization of Sphingomyelin and Dihydrosphingomyelin of Human Lens Membranes," *Ophthalmic Res.*, 29(4):191-206, 1997.

Chu, E., et al., *Physician's Cancer Chemotherapy Drug Manual*, Jones and Bartlett Publishers, Massachusetts, 2002, Ch. 4, "Common Chemotherapy Regimens in Clinical Practice," pp. 387-461.

Deamer, D. et al., "Large Volume Liposomes by an Ether Vaporization Method," *Biochim. et Biophys. Acta* 443:629-634, 1976.

DeFrees, S., et al., "Sialyl Lewis x-Liposomes as a Multivalent Ligand and Inhibitor of E-Selection Mediated Cellular Adhesion," *J. Am. Chem. Soc.*, 118:6101-6104, 1996.

U.S. Appl. No. 08/316,394, filed Sep. 30, 1994, Ansell.

U.S. Appl. No. 08/996,783, filed Dec. 23, 1997, Ansell.

Deutsch, H., et al., "Synthesis of Congeners and Prodrugs. 3. Water-soluble Prodrugs of Taxol with Potent Antitumor Activity," *J Med Chem.*, 32(4):788-92, Apr. 1989.

Dumontet, C. et al., "Mechanisms of Action of and Resistance to Antitubulin Agents: Microtubule Dynamics, Drug Transport, and Cell Death," *J. Clin. Oncol.* 17(3):1061-1070, Mar. 1999.

Fenske, D., et al., "Ionophore-mediated Uptake of Ciprofloxacin and Vincristine into Large Unilamellar Vesicles Exhibiting Transmembrane Ion Gradients," *Biochim Biophys Acta.*, 1414(1-2):188-204, Nov. 11, 1998.

Fiebig, H., et al., *Tumor Models in Cancer Research*, Teicher, B.A. (ed.), Humana Press Inc. Totowa, 2002, Ch. 7, "Human Tumor Xenografts and Explants," pp. 113-137.

Fraley, R., et al., "Entrapment of a Bacterial Plasmid in Phospholipid Vesicles: Potential for Gene Transfer," *Proc Natl Acad Sci U S A.*, 76(7):3348-52, Jul. 1979.

Gruner, S., chapter 1 "Materials Properties of Liposomal Bilayers," in Ostro, M.J. (ed.), *Liposomes: From Biophysics to Therapeutics*, Marcel Dekker, New York, 1993, pp. 1-38.

Heath, T., "Covalent Attachment of Proteins to Liposomes," *Methods in Enzymology* 149:111-119, 1987.

Hope, M. et al., "Production of Large Unilamellar Vesicles by a Rapid Extrusion Procedure. Characterization of Size Distribution, Trapped Volume and Ability to Maintain a Membrane Potential," *Biochim. et Biophys. Acta* 812:55-65, 1985.

Hope, M. et al., "Generation of Multilamellar and Unilamellar Phospholipid Vesicles," *Chemistry and Physics of Lipids* 40:89-107, 1986.

Karlsson, A., et al., "Molecular Species of Sphingomyelin: Determination by High-Performance Liquid Chromatography/mass Spectrometry with Electrospray and High-Performance Liquid Chromatography/tandem Mass Spectrometry with Atmospheric Pressure Chemical Ionization," *J Mass Spectrom.*, 33(12):1192-8, Dec. 1998.

King, R.E., *Remington's Pharmaceutical Sciences*, 17$^{th}$ Ed., Mack Publishing Co., Philadelphia, PA, 1985, Part 8, "Pharmaceutical Preparations and Their Manufacture," pp. 1409-1677.

Kirpotin, D., et al., "Liposomes with Detachable Polymer Coating: Destabilization and Fusion of Dioleoylphosphatidylethanolamine Vesicles Triggered by Cleavage of Surface-Grafted Poly(ethylene glycol)," *FEBS Lett.*, 388(2-3):115-8, Jun. 17, 1996.

Klibanov, A., et al., "Long-Circulating Liposomes: Development and Perspectives," *J. Liposome Res.*, 2(3):321-334, 1992.

Koynova, R., et al., "Phases and Phase Transitions of the Sphingolipids," *Biochim Biophys Acta.*, 1255(3):213-36, Apr. 6, 1995.

Kuikka, M., et al., "Membrane Properties of D-erythro-N-acyl Sphingomyelins and Their Corresponding Dihydro Species," *Biophys J.*, 80(5):2327-37, May 2001.

Lasch, J., et al., *Liposomes: A Practical Approach*, (2$^{nd}$ ed.—Tochilin et al.) Oxford University Press, New York, 2003, Ch. 1, "Preparation of Liposomes," pp. 3-29.

Leonetti, J-P. et al., "Antibody-Targeted Liposomes Containing Oligodeoxyribonucleotides Complementary to Viral RNA Selectively Inhibit Viral Replication," *Proc. Natl. Acad. Sci. USA* 87:2448-2451, Apr. 1990.

Madden, T., et al., "The Accumulation of Drugs within Large Unilamellar Vesicles Exhibiting a Proton Gradient: a Survey," *Chem Phys Lipids.*, 53(1):37-46, Mar. 1990.

Marsh, D., *CRC Handbook of Lipid Bilayers*, CRC Press, Boca Raton, FL. 1990, pp. 139-144.

Mathew, A., et al., "Synthesis and Evaluation of Some Water-soluble Prodrugs and Derivatives of Taxol with Antitumor Activity," *J Med Chem.*, 35(1):145-51, Jan. 1992.

Mayer, L., et al., "Solute Distributions and Trapping Efficiencies Observed in Freeze-thawed Multilamellar Vesicles," *Biochim Biophys Acta.*, 817(1):193-6, Jul. 11, 1985.

Mayer, L., et al., "Vesicles of Variable Sizes Produced by a Rapid Extrusion Procedure," *Biochim. et Biophys. Acta* 858:161-168, 1986.

Mayer, L., et al., "Influence of Vesicle Size, Lipid Composition, and Drug-to-lipid Ratio on the Biological Activity of Liposomal Doxorubicin in Mice," *Cancer Res.*, 49(21):5922-30, Nov. 1, 1989.

Mayer, L., et al., "Characterization of Liposomal Systems Containing Doxorubicin Entrapped in Response to pH Gradients," *Biochim Biophys Acta.*, 1025(2):143-51, Jun. 27, 1990.

Merck Index, 11$^{th}$ ed. 1989, Entry Nos. 9887, 9891, & 9893.

Ollila, F., et al., "Partitioning of Triton X-100, Deoxycholate and C(10)EO(8) into Bilayers Composed of Native and Hydrogenated Egg Yolk Sphingomyelin," *Biochim Biophys Acta.*, 1564(1):281-8, Aug. 19, 2002.

Plowman, J. et al. *Anticancer Drug Development Guide: Preclinical Screening, Clinical Trials, and Approval*, (Ed. Teicher, B.) Humana Press Inc., Totowa, 1997, "Human Tumor Xenograft Models in NCI Drug Development," pp. 101-125.

Ramstedt, B., et al., "Analysis of Natural and Synthetic Sphingomyelins Using High-Performance Thin-layer Chromatography," *Eur J Biochem.*, 266(3):997-1002, Dec. 1999.

Renneisen, K. et al., "Inhibition of Expression of Human Immunodeficiency Virus-1 in Vitro by Antibody-Targeted Liposomes Containing Antisense RNA to the *env* Region," *J. Biol. Chem.* 265(27):16337-16342, Sep. 1990.

Sapra, P., et al., "Ligand-targeted Liposomal Anticancer Drugs," *Prog Lipid Res.*, 42(5):439-62, Sep. 2004.

Schneider, P., et al., "Sphingomyelinase in Normal Human Spleens and in Spleens from Subjects with Niemann-Pick Disease," *J Lipid Res.*, 8(3):202-9, May 1967.

Szoka F., "Comparative Properties and Methods of Preparation of Lipid Vesicles (Liposomes)," *Ann. Rev. Biophys. Bioeng.* 9:467-508, 1980.

Webb, M., et al., "Sphingomyelin-cholesterol Liposomes Significantly Enhance the Pharmacokinetic and Therapeutic Properties of Vincristine in Murine and Human Tumour Models," *Br J Cancer.*, 72(4):896-904, Oct. 1995.

Williams, K. et al., "Low Density Lipoprotein Receptor-Independent Hepatic Uptake of a Synthetic, Cholesterol-Scavenging Lipoprotein: Implications for the Treatment of Receptor-Deficient Atherosclerosis," *Proc. Natl. Acad. Sci. USA* 85:242-246, Jan. 1988.

Wood, P. et al., "Human Plasma Sphingomyelins," *Proc Soc Exp Biol Med.*, 115:990-2, Apr. 1964.

Wozniak, A., et al., "Randomized Trial Comparing Cisplatin with Cisplatin plus Vinorelbine in the Treatment of Advanced Non-small-cell Lung Cancer: a Southwest Oncology Group study," *J Clin Oncol.*, 16(7):2459-65, Jul. 1998.

Yuan, F., et al., "Microvascular Permeability and Interstitial Penetration of Sterically Stabilized (stealth) Liposomes in a Human Tumor Xenograft," *Cancer Res.*, 54(13):3352-6, Jul. 1, 1994.

Zalipsky, S., "Synthesis of an End-group Functionalized Polyethylene Glycol-lipid Conjugate for Preparation of Polymer-grafted Liposomes," *Bioconjug Chem.*, 4(4):296-9, Jul.-Aug. 1993.

Zalipsky, S., et al., "Long Circulating, Cationic Liposomes Containing Amino-PEG-Phosphatidylethanolamine," *FEBS Lett.*, 353(1):71-4, Oct. 10, 1994.

Zalipsky, S., *In: Stealth Liposomes*, (Lasic and Martin, Eds.) CRC Press, Boca Raton, FL, 1995, Ch. 9, "Polyethylene Glyco-Lipid Conjugates," pp. 93-102.

Ayengar, N., et al., "Effect of 2 Hydroxy Substituted Cholesterol Derivatives on Mono Layer Condensation and Membrane Closure," *Chemistry and Physics of Lipids*, 25(2):203-208, 1979.

Nyholm, T., et al., "Properties of Palmitoyl Phosphatidylcholine, Sphingomyelin, and Dihydrosphingomyelin Bilayer Membranes as Reported by Different Fluorescent Reporter Molecules," *Biophys J.*, 84(2 Pt 1):987-97, Feb. 2003.

* cited by examiner

LIPOSOMAL FORMULATIONS COMPRISING DIHYDROSPHINGOMYELIN AND METHODS OF USE THEREOF

CROSS-REFERENCES TO RELATED APPLICATIONS

This application claims the benefit under 35 U.S.C. §119 (e) of U.S. Provisional Patent Application No. 60/571,712, filed May 17, 2004; and U.S. Provisional Patent Application No. 60/631,997, filed Nov. 30, 2004, where these provisional applications are incorporated herein by reference in their entireties.

BACKGROUND OF THE INVENTION

1. Field of the Invention

The present invention relates to liposomes, liposomal compositions, and methods suitable for the delivery of active agents.

2. Description of the Related Art

A major challenge facing medical science and the pharmaceutical industry, in particular, is to develop methods for providing therapeutic agents to appropriate tissues or cells at a sufficient dosage to provide a therapeutic benefit, without prohibitively harming the patient being treated. Accordingly, it is an important goal of the pharmaceutical industry to develop drug delivery devices and methods that provide increased efficacy with decreased associated toxicity. A variety of different general approaches have been taken, with various degrees of success. These include, e.g., the use of implantable drug delivery devices, the attachment of targeting moieties to therapeutic compounds, and the encapsulation of therapeutic compounds in carriers, e.g., liposomes, to modulate drug biodistribution and the duration of drug exposure.

Liposomes are particulate carriers and, hence, tend to remain within the blood compartment, as they are not able to extravasate across the continuous endothelial lining present in most blood vessels. At disease sites, however, the blood vessels may be leaky, allowing liposome extravasation and accumulation in the interstitial space. In tumors, for example, the immature neovasculature tends to exhibit pores or defects that can allow liposomes of appropriate size to exit the blood vessels (Yuan et al., *Cancer Research* 54: 3352-3356, 1994). Similarly, at sites of infection or inflammation, the endothelial permeability barrier can be compromised, allowing liposomes to accumulate in these regions. In contrast, the blood vessels present in most normal, healthy tissues tend to have continuous endothelial linings. Hence, liposomal delivery can reduce drug exposure to these areas. Exceptions are the organs of the mononuclear phagocyte system (MPS), such as the liver and spleen, where fenestrated capillaries are present.

In efforts to develop more effective therapeutic treatments, a variety of compounds have been formulated in liposomes. For example, many anticancer or antineoplastic drugs have been encapsulated in liposomes. These include vinca alkaloids, alkylating agents, nitrosoureas, platinum co-ordination complexes, antimetabolites, anthracyclines, and camptothecins. Studies with liposomes containing anthracycline antineoplastics have clearly shown reduction of cardiotoxicity and prolonged survival of tumor bearing animals compared to controls receiving free drug. In addition, liposomal formulations of antibiotics, anti-inflammatory agents, and antifungal drugs have been described.

In order to achieve efficient drug delivery to disease sites using liposomal carriers, however, the liposomes should exhibit a relatively long plasma circulation half-life to increase the likelihood of extravasate during passage through the site. In addition, drug release from the liposomes should be slow to reduce drug loss prior to carrier accumulation at the disease site. Further, drug activity is often dependent on the duration of drug exposure. In order to optimize efficacy, therefore, slow drug release from the liposomes may be required.

Considerable efforts have been made to identify liposomal carrier compositions that show slow clearance from the blood, and long-circulating carriers have been described in numerous scientific publications and patents. Such long-circulating carriers may employ polymer coatings, e.g., polyethylene glycol (PEG), to reduce uptake by the MPS (reviewed by Allen and Stuart in *Liposomes: Rationale Design*, Janoff, A. S. (ed), Marcel Dekker Inc., New York (1999); Allen et al., *Biochimica et Biophysica Acta* 1066: 29-36, 1991) or may employ specific lipid compositions, such as ganglioside (U.S. Pat. No. 4,837,028; Allen and Choon, *FEBS Letters*, 223: 4246, 1987), or sphingomyelin and cholesterol (U.S. Pat. No. 5,543,152; U.S. Pat. No. 5,741,516; U.S. Pat. No. 5,814,335). Efforts have also been made to control drug leakage or release rates from liposomal carriers, using for example, various lipid components or a transmembrane potential to control release (U.S. Pat. No. 5,077,056). Alternatively, drug release rates may be controlled by precipitation of the drug within the liposomal carriers (U.S. Patent Publication No. 2002/0119990-A1) as indicated by the previous studies, not all lipid formulations are equal for drug delivery purposes and extensive research continues into formulations which demonstrate preferred characteristics for drug loading and storage, drug administration, pharmacokinetics, biodistribution, leakage rates, tumor accumulation, toxicity profile, and the like. Accordingly, while numerous liposomes and lipid-based drug delivery vehicles have been developed, there is clearly still a need in the art for improved liposomal compositions, including liposomes that provide reduced levels of clearance and slow drug release.

BRIEF SUMMARY OF THE INVENTION

The present invention includes liposomes, liposomal compositions and related methods and kits. In one embodiment, the invention provides a liposome comprising dihydrosphingomyelin (DHSM) wherein said DHSM constitutes at least 20% or at least 50% of total phospholipid present in said liposome.

In various embodiments of liposomes of the invention, the DHSM N-acyl chain consists of 12 to 24 carbon atoms. In one particular embodiment, the DHSM N-acyl chain consists of 16 carbon atoms.

In other related embodiments, the DHSM is selected from the group consisting of: D-erythro-N-palmityl-dihydrosphingomyelin (16:0-DHSM), D-erythro-N-stearyl-dihydrosphingomyelin (18:0-DHSM), D-erythro-N-arachidyl-dihydrosphingomyelin, D-erythro-N-heneicosanyl-dihydrosphingomyelin, D-erythro-N-behenyl-dihydrosphingomyelin, D-erythro-N-tricosanyl-dihydrosphingomyelin, D-erythro-N-lignoceryl-dihydrosphingomyelin. Alternatively the DHSM may consists of a mixture of N-acyl chains, such as the mixture of N-acyl chains present in brain sphingomyelin, egg sphingomyelin or milk sphingomyelin, or such mixtures of N-acyl chains derived from such natural sources but where any unsaturated N-acyl chain is saturated. In particular embodiments, the DHSM is brain DHSM, egg DHSM, or milk DHSM.

In one embodiment, the DHSM is prepared by hydrogenation of a synthetic sphingomyelin. In another embodiment the DHSM is prepared by hydrogenation of a natural sphingomyelin, such as brain sphingomyelin, egg sphingomyelin or milk sphingomyelin.

In yet another embodiment, the DHSM N-acyl and sphingosine chains comprise carbon chains that are not different in length by more than four carbon atoms.

In a further related embodiment, at least 50% of the DHSM comprises DHSM wherein the N-acyl and dihydrosphingosine comprise carbon chains that are not different in length by more than four carbon atoms. In certain embodiments of the invention, the liposomes further comprise cholesterol. In particular embodiments, the DHSM and cholesterol are present at a molar ratio from 75/25 (mol/mol) DHSM/cholesterol to 25/75 (mol/mol) DHSM/cholesterol. In particular embodiments, the DHSM and cholesterol are present at a molar ratio from 60/40 (mol/mol) DHSM/cholesterol to 40/60 (mol/mol) DHSM/cholesterol. In further embodiments, the DHSM and cholesterol are present at a molar ratio of either about 55/45 (mol/mol) or about 50/50 (mol/mol) DHSM/cholesterol.

In certain embodiments of the invention, the liposomes comprise DHSM, cholesterol and other phospholipids or derivatized phospholipids, wherein DHSM comprises at least 20% or at least 50% of the total phospholipid present, and cholesterol is present at a molar ratio from 75/25 (mol/mol) total phospholipid/cholesterol to 25/75 (mol/mol) total phospholipid/cholesterol. In particular embodiments, the liposomes comprise DHSM, cholesterol and other phospholipids or derivatized phospholipids, wherein DHSM comprises at least 20% or at least 50% of the total phospholipid present, and cholesterol is present at a molar ratio from 60/40 (mol/mol) total phospholipid/cholesterol to 40/60 (mol/mol) total phospholipid/cholesterol. In particular embodiments, total phospholipid and cholesterol are present at a molar ratio of about 55/45 (mol/mol) total phospholipid/cholesterol or about 50/50 (mol/mol) total phospholipid/cholesterol.

In another embodiment, more than 10%, 20%, 30%, 40%, 50%, 60%, 70%, 80% or 90% of the DHSM N-acyl chains are saturated.

In other embodiments, the invention provides a liposomal composition comprising a liposome of the invention and a therapeutic compound.

In one embodiment, the therapeutic compound is an antineoplastic agent. In specific embodiments, the antineoplastic agent is a vinca alkaloid, a camptothecin, an anthracycline, NK611, an etoposide, or a taxane. In particular embodiments, the vinca alkaloid is vincristine, vinblastine, or vinorelbine. In other embodiments, the camptothecin is topotecan or irinotecan, or SN-38. In other embodiments, the taxane is paclitaxel or docetaxel.

In yet another related embodiment, the invention includes methods of delivering a therapeutic agent to a patient, comprising administering to the patient a pharmaceutical composition comprising a liposome-encapsulated therapeutic agent, wherein said liposome comprises DHSM and wherein at least 20% or at least 50% of the total phospholipids present in said liposome is DHSM. In one embodiment, the liposome used according to the method further comprises cholesterol. In particular embodiments, the DHSM and cholesterol are present at a molar ratio from 75/25 (mol/mol) DHSM/cholesterol to 25/75 (mol/mol) DHSM/cholesterol. In particular embodiments, the DHSM and cholesterol are present at a molar ratio from 60/40 (mol/mol) DHSM/cholesterol to 40/60 (mol/mol) DHSM/cholesterol, or are present at a molar ratio of either about 55/45 (mol/mol) or about 50/50 (mol/mol) DHSM/cholesterol.

In a further embodiment, the liposomes used according to the method comprise DHSM, cholesterol and other phospholipids or derivatized phospholipids, wherein DHSM comprises at least 20% or at least 50% of the total phospholipid present, and cholesterol is present at a molar ratio from 75/25 (mol/mol) total phospholipid/cholesterol to 25/75 (mol/mol) total phospholipid/cholesterol. In particular embodiments, the liposomes comprise DHSM, cholesterol and other phospholipids or derivatized phospholipids, wherein DHSM comprises at least 20% or at least 50% of the total phospholipid present, and cholesterol is present at a molar ratio from 60/40 (mol/mol) total phospholipid/cholesterol to 40/60 (mol/mol) total phospholipid/cholesterol, and in further embodiments, total phospholipid and cholesterol are present at either about 55/45 (mol/mol) total phospholipid/cholesterol or about 50/50 (mol/mol) total phospholipid/cholesterol.

In related embodiments, the therapeutic agent used according to the method of the invention is an antineoplastic agent. In particular embodiments, the antineoplastic agent is one of the particular agents described above.

In another related embodiment, the invention includes a method of treating a cancer in a mammal, comprising administering to the mammal a pharmaceutical composition comprising a liposome-encapsulated therapeutic agent, wherein said liposome comprises DHSM and wherein the DHSM comprises at least 20% or at least 50% of the phospholipids present in said liposome. In a particular embodiment, the liposome further comprises cholesterol. In particular embodiments, the ratio of DHSM or total phospholipid to cholesterol is any range or amount described herein.

In various embodiments, methods of the invention are used to treat a variety of cancers, including a leukemia or lymphoma, or a solid tumor, such as solid tumors of the lung, mammary, and colon. Such treatments can be at first presentation of the cancer or in patients who have relapsed after previous therapy.

The invention further provides a method of making a pharmaceutical composition, comprising preparing a liposome comprising the dihydrosphingomyelin and loading the prepared liposome with a therapeutic compound.

In a related embodiment, the invention also provides a method of manufacturing a pharmaceutical composition, comprising loading a liposome comprising dihydrosphingomyelin with a therapeutic compound.

In an additional embodiment, the invention includes a kit comprising: a liposome comprising DHSM, wherein said DHSM comprises at least 20% or at least 50% of the phospholipids present in said liposome, and a therapeutic compound.

In a further related embodiment, the invention provides a method of loading a therapeutic agent into a liposome, comprising: incubating a liposome comprising DHSM and having an encapsulated medium comprising $MnSO_4$, wherein said DHSM comprises at least 20% or at least 50% of the total phospholipids of the liposome, with an external solution comprising said therapeutic agent and an ionophore at a temperature greater than 60° C. to form a therapeutic agent-loaded liposome. In particular embodiments, $MnSO_4$ is present at a concentration equal to or greater than 300 mM. In one embodiment, $MnSO_4$ is present at a concentration of 600 mM. In related embodiments, the temperature at which the therapeutic agent is loaded into the liposomes is less than or equal to 70° C. In a specific embodiment, the temperature is 70° C.

In yet a further related embodiment, the present invention includes a liposome comprising DHSM, wherein said DHSM constitutes at least 20% or at least 50% (molar basis) of total phospholipid present in said liposome, and wherein the interior of said liposome comprises $MnSO_4$. In particular embodiments, the liposome may further comprise an active agent. In one embodiment, the active agent is topotecan.

In another embodiment, the present invention provides a composition comprising empty liposomes and liposomes containing an active agent, wherein said liposomes comprising an active agent comprise $MnSO_4$ and DHSM, wherein said DHSM constitutes at least 20% or at least 50% (molar basis) of total phospholipid present in said liposomes. In one embodiment, the active agent is topotecan.

In further related embodiments, the invention includes methods of using a liposomal composition of the present invention to treat a disease, e.g., tumor, by administering said liposomal composition to a patient in need thereof.

The invention further includes kits comprising a liposome or liposomal composition of the present invention.

BRIEF DESCRIPTION OF THE DRAWINGS

FIG. 8A illustrates vincristine retention; FIG. 8B depicts NK611 retention; and FIG. 8C provides topotecan retention.

DETAILED DESCRIPTION OF THE INVENTION

Figure 1:
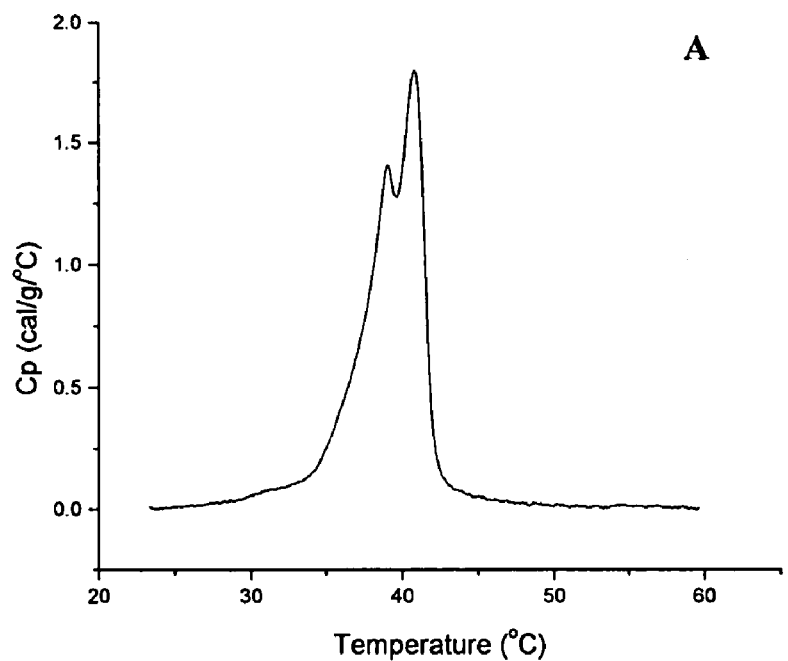
FIG. 1 depicts concentration-normalized differential scanning calorimetry (DSC) data for egg sphingomyelin (ESM) (A) or egg dihydrosphingomyelin (EDHSM) (B). Samples were scanned from 20 to 60° C. at a scan rate of 5° C./hr.
Figure 1:
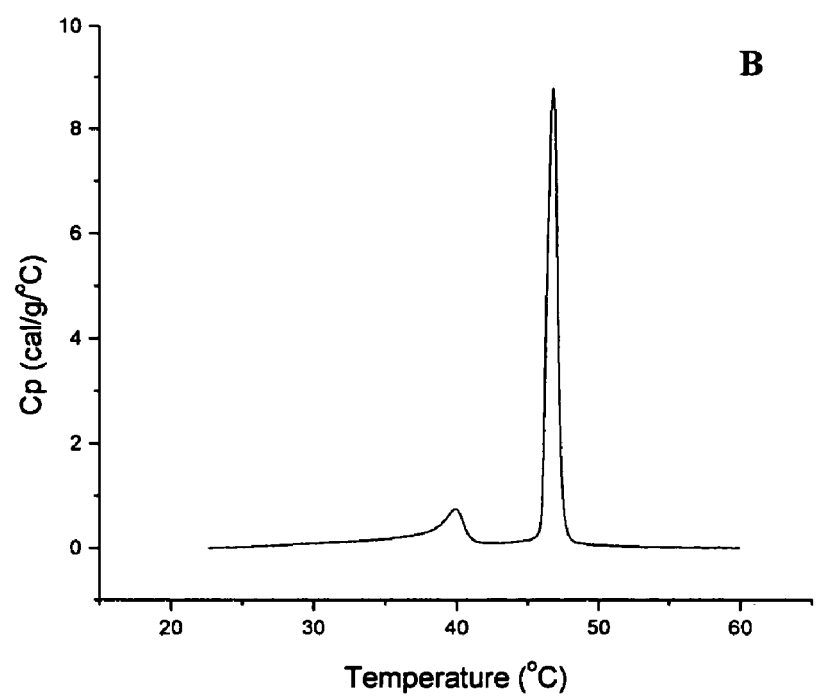

The present invention includes novel liposomes and liposomal compositions comprising therapeutic agents, as well as methods of preparing and using such liposomes and liposomal compositions to deliver therapeutic agents and treat diseases, including cancer. The invention is fundamentally based on the surprising discovery that liposomes comprising dihydrosphingomyelin (DHSM) have markedly altered properties as compared to liposomes comprising sphingomyelin (SM) and/or other phospholipids. Most notably, liposomes prepared using DHSM show significantly increased retention of active agents encapsulated within the liposomes, both in vitro and in vivo, as compared to liposomes prepared using SM and/or other phospholipids. This finding was entirely unexpected given the structural characteristics and physical properties of SM and DHSM, including those summarized below. In addition, liposomes comprising DHSM exhibit longer plasma circulation half-lives compared to similar liposomes comprising SM. Associated with these changes in pharmacokinetics, liposomes comprising DHSM and topotecan were found to exhibit greater antitumor activity compared to similar liposomes comprised of SM in murine models of human tumors.

Sphingomyelin comprises two variable components: the sphingosine base (long chain base) and the long chain N-acyl residue (fatty acid chain). The three main structures of long chain bases present in sphingomyelin include: 4-sphingenine (sphingosine); sphinganine, or, in its trivial name, dihydrosphingosine; and 4-D-hydroxy sphingosine (phytosphingosine). Sphingosine (trans-D-erythro-1,3-dihydroxy-2-amino-4-octadecene), also described as trans-2S,3R)-2-amino-4-octadecene-1,3-diol, is the main long chain base found in mammals; dihydrosphingosine (trans-D-erythro, 1,3-dihydroxy-2-amino-4-octadecane or (2S,3R)-2-amino-octadecane-1,3-diol) and phytosphingosine (1,3,4-trihydroxy-D-ribo-2-amino-(2S,3R,4R)-2-amino-octadenane-1, 3,4-triol) are also found in eukaryotic sphingomyelin, but generally to a much lesser extent. For example, in cultured mammalian cells, only 5-10% of sphingomyelin contains the dihydrosphingosine base (Ramstedt et al. European Journal of Biochemistry, 266: 997-1002 (1999)). An exception is the human lens membranes where dihydrosphingomyelin accounts for about 50% of the phospholipid present (Byrdwell and Borchman, Ophthalmic Research, 29: 191-206 (1997)). Sphingosine comprises a trans double bond between carbons 4 and 5 of the sphingosine chain, whereas dihydrosphingosine lacks this trans double bond. Representative examples of structures of sphingomyelins comprising sphingosine or dihydrosphingosine are as follows:

Y., In Physiology of Membrane Fluidity, Vol. 1. Shinitsky, M., ed. CRC Press, Boca Raton, Fla. 131-174 (1984)). Greater than 93% of egg sphingomyelin has a saturated N-acyl chain, as compared to phosphatidylcholines (PCs), which typically have 23-47% saturated chains (e.g., soy PC is 23% saturated; egg PC is 45% saturated).

Detailed structural analysis of sphingomyelins derived from various natural sources, including egg, milk, and brain sphingomyelin, confirms that the N-acyl chain is largely saturated or monounsaturated. In addition, the vast majority of naturally occurring sphingomyelin comprises a monounsaturated long chain base (e.g. sphingosine base). Specifically, the most common long chain bases detected were 16:1, 17:1, 18:1 and 19:1, whereas the most common N-acyl chains detected were 16:0, 22:0, 23:0, and 24:0 (Karlsson, A., et al., *Journal of Mass Spectrometry* 33:1192-1198 (1998)).

As used herein, the general term sphingomyelin (SM) includes SMs having any long chain base or N-acyl chain, including those described above. The term dihydrosphingomyelin (DHSM) refers to SMs comprising a sphinganine (i.e., dihydrosphingosine) long chain base and, therefore, lacking the trans double bond in the long chain base. DHSM may contain one or more cis double bonds in the N-acyl chain. In a preferred embodiment, DHSM contains both fully saturated N-acyl chain and a saturated long base chain. In addition, the term hydrogenated SM refers generally to SMs that have been hydrogenated by any method available in the art.

Dihydrosphingomyelin is more specifically defined herein as any N-acyl-sphinganyl-1-O-phosphorylcholine derivative. Sphinganine is a natural product that typically is composed primarily of D-erythro-2-amino-octadecane-1,3-diol, although material from some sources may also contain significant amounts of D-erythro-2-amino-heptadecane-1,3-diol. The sphinganine backbone of dihydrosphingomyelin is

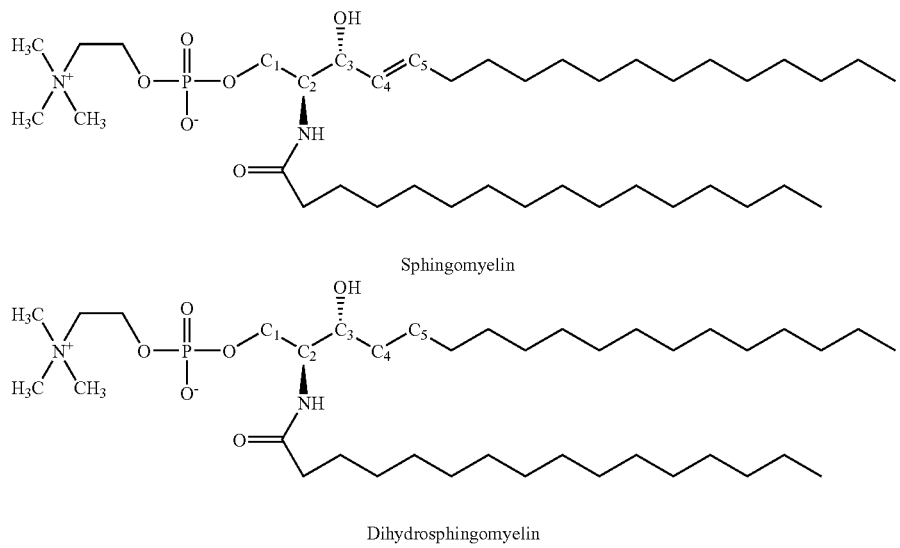

Sphingomyelin

Dihydrosphingomyelin

The N-acyl composition of sphingomyelin of most mammalian sources is characterized by a relatively high content of long-chain saturated or monounsaturated acyl chains and a low content of polyunsaturated acyl chains. In most mammalian tissues, palmitic acid (C16:0) is the prevalent fatty acid, followed in decreased abundance by nervonic acid (24:1), lignoceric acid (24:0), and behenic acid (C22:0) (Barenholz, defined here more generally to include any D-erythro-2-amino-alkane-1,3-diol wherein the alkane is a linear chain 12 to 24 carbon atoms in length, or any mixture thereof.

The presence of the trans double bond between carbons 4 and 5 in the sphingosine base has been shown to impart specific structural and physiological properties upon SMs. For example, analysis of the monolayer properties of SM and DHSM showed that their packing properties are very similar, except that the expanded-to-condensed phase transition (crystallization) occurred at a lower pressure for DHSM as compared to SM (Kuikka, M. et al., *Biophysical Journal* 80:2327-2337 at 2335 (2001)). Furthermore, it has been shown that the surface potential of DHSM monolayers is reduced compared with SM monolayers, possibly originating from an inducible dipole due to the trans double bond being present in SM but absent in DHSM (Kuikka, M. et al., at 2335 (2001)).

Interestingly, it was demonstrated that 16:0-DHSM was degraded much faster by sphingomyelinase from *Staphylococcus aureus* than 16:0-SM, and a ten-fold difference in enzyme activity was needed to produce a comparable hydrolysis rate (Kuikka, M. et al., *Biophysical Journal* 80:2327-2337 at 2330-2331 (2001)). The authors suspected that packing heterogeneity (defects) similar to those seen at boundaries between ordered and disordered membrane domains were responsible for the increased susceptibility of DHSM to enzymatic degradation. Without wishing to be bound by any particular theory, it is noted that the increased susceptibility to enzymatic degradation suggests that, upon administration to a patient, liposomes comprising DHSM are susceptible to more rapid clearance from the bloodstream and/or more rapid release of encapsulated compounds, e.g., drugs, as compared to liposomes comprising SM having the trans double bond.

The presence of the trans-double bond between carbon atoms 4 and 5 of the sphingenine moiety has been shown to have little effect on the character of the gel-liquid crystalline phase transition of SMs. For example, the difference between the Tm values for 16:0-SM and 16:0-DHSM is only 6.5° C. (Kuikka, M. et al., *Biophysical Journal* 80:2327-2337 at 2331-2333 (2001)). In comparison, the difference in Tm between a phosphatidylcholine (PC) possessing saturated (16:0) fatty acid chains and monounsaturated (16:1) fatty acid chains is approximately 77° C. (16:0 PC, Tm=41° C.; 16:1 PC, Tm=−36° C.) (Marsh, D. CRC Handbook of Lipid Bilayers, CRC Press, Boca Raton, Fla. (1990) at p. 139 and p. 144). The relatively small effect on Tm value from hydrogenation of the trans double bond in SM has been ascribed to the position of this bond in the structurally ordered interface, where it is not expected to influence considerably the packing order of the hydrocarbon chains and thus effect the chain order-disorder transition (Konova, R. and Caffrey, M., *Biochim. Biophys. Acta* 1255:213-236 (1995).

Furthermore, the presence of the trans double-bond in DHSM does not appear to affect its interaction with cholesterol in mixed monolayers when cholesterol is present at 50 mol % or less. Studies measuring cholesterol desorption from monolayers to cyclodextrin acceptors in the subphase, which was used as a measure of how well cholesterol interacts with other lipids in a mixed monolayer, revealed that the desorption rate was practically zero using either 16:0-SM or 16:0-DHSM when the cholesterol concentration in the mixed monolayer was 50 mol % (Kuikka, M. et al., *Biophysical Journal* 80:2327-2337 (2001), p. 2330, col. 2, lines 8-29).

Based on these studies demonstrating little impact of the presence or absence of the trans double bond on packing density or Tm, it was extremely surprising to discover that hydrogenation of this trans double bond resulted in liposomes having increased retention of active agents encapsulated within. Furthermore, the magnitude of the observed effect was also very surprising, given that naturally-occurring sphingomyelin comprises only the single trans double bond and generally either no cis double bonds or only one cis double bond. Accordingly, it was surprising to discover that liposomal compositions prepared from liposomes comprising DHSM and a therapeutic agent provide unexpected advantages in drug delivery, including both increased retention of the therapeutic agent in the liposome in vitro, increased plasma drug retention in vivo, long plasma circulation half-lives for both the liposomes and drug, and increased antitumor activity against human tumor xenografts in a murine model.

A. Liposomes Comprising Dihydrosphingomyelin

The present invention includes liposomes comprising DHSM or hydrogenated SM. As used herein, a liposome is a structure having lipid-containing membranes enclosing an aqueous interior. Liposomes may have one or more lipid membranes. The invention contemplates both single-layered liposomes, which are referred to as unilamellar, and multi-layer liposomes, which are referred to as multilamellar.

In various embodiments, the invention contemplates liposomes comprising any naturally occurring or synthetically produced DHSM, including those described in further detail infra. These liposomes may further comprise one or more additional lipids and/or other components such as cholesterol. Specific embodiments of liposomes of the invention and their various components are described below.

1. Sphingomyelin

The liposomes of the present invention comprise dihydrosphingomyelin (DHSM) or hydrogenated sphingomyelin, including, but not limited to, any naturally occurring, semi-synthetic or synthetic DHSM described herein.

Naturally occurring SMs have the phosphocholine head group linked to the hydroxyl group on carbon one of a long-chain base and have a long and highly saturated acyl chain linked to the amide group on carbon 2 of the long-chain base (reviewed in Barenholz, Y. in *Physiology of Membrane Fluidity*, Vol. 1. M. Shinitsky, editor. CRC Press, Boca Raton, Fla. 131-174 (1984)). In cultured cells, about 90 to 95% of the SMs contain sphingosine (1,3-dihydroxy-2-amino-4-octadecene), which contains a trans-double bond between C4 and C5, as the long-chain base, whereas most of the remainder have sphinganine (1,3-dihydroxy-2-amino-4-octadecane) as the base and lack the trans double bond between carbons 4 and 5 of the long chain base. The latter SMs are called dihydrosphingomyelins (DHSM).

Other bases varying in length, degree of hydroxylation, and branching are also found in nature. The enantiomeric configuration of the sphingoid base in natural SMs is D-erythro (2S,3R). Synthetically produced SMs may comprise either the D-erythro or L-erythro configuration or a mixture of both.

Natural SMs usually constitute a mixed population with the amide-linked acyl chain differing widely in length (generally from 16-24 carbons). The SM N-acyl chain composition varies between tissues, although a common feature of naturally occurring SMs is that the chains are usually long. Most tissues contain SMs with 16:0, 18:0, 22:0, 24:0 and $24:1^{cis\Delta 15}$ N-acyl chains. In SM, there is also a high frequency of saturated amide-linked acyl chains with an average of only 0.1-0.35 cis-double bonds per molecule. When present, the cis-double bond in natural SM is typically located far away from the interface, as in nervonic acid ($24:1^{cis\Delta 15}$) with a double bond at $C_{15}$. The interfacial region of SM has an amide group, a free hydroxyl on $C_3$ and the trans-double bond between $C_4$ and $C_5$ in this region.

The N-acyl composition of SM isolated from natural sources is provided in Table 1. Reference in Table 1 to saturated or unsaturated is specific for the fatty acid chain of sphingomyelin derived from the various sources and does not indicate the presence or absence of the trans double bond in the long chain base. For consistency with the nomenclature used with other phospholipids, such as phosphatidylcholine, the N-acyl chains on SM are sometimes referred to as fatty acids. However it is to be understood that these acyl chains are linked to the sphingosine base via an amide bond and not via an ester bond such as is present with most other phospholipids.

TABLE 1

N-Acyl chain compositions of sphingomyelin (wt % of the total) from various sources

| | Tissue Derived | | | | | |
|---|---|---|---|---|---|---|
| N-Acyl Chain Composition | Egg SM[1] | Egg SM[2] | Brain SM[1] | Brain SM[2] | Milk SM[1] | Milk SM[2] |
| SATURATED | | | | | | |
| 16:0 | 84% | 66% | 2% | 3% | 19% | 14% |
| 18:0 | 6% | 10% | 46% | 42% | 3% | 3% |
| 20:0 | 2% | 4% | 5% | 6% | 1% | 1% |
| 22:0 | 4% | 6% | 7% | 7% | 19% | 22% |
| 23:0 | | 2% | | 3% | 33% | 32% |
| 24:0 | 4% | 5% | | 6% | 20% | 19% |
| SUBTOTAL | 100% | 93% | 60% | 67% | 95% | 91% |
| UNSATURATED | | | | | | |
| 18:1 | | 1% | | | | 1% |
| 20:4 | | | | 2% | | |
| 22:1 | | 1% | | 3% | | |
| 23:1 | | | | 3% | | |
| 24:1 | | 3% | 6% | 27% | 3% | 5% |
| SUBTOTAL | | 5% | 6% | 33% | 5% | 6% |
| UNKNOWN | | | | | | |
| Other | | | | 34% | | |
| TOTAL | 100% | 98% | 100% | 100% | 100% | 97% |

[1]Avanti - based on Wood & Holton (1964) Proc. Soc. Exptl. Biol. Med 115, 990
[2]based on Ramstedt B, Leppimaki P, Axberg M, Slotte JP (1999) Analysis of natural and synthetic sphingomyelins using high-performance thin-layer chromatography. Eur J Biochem. 266(3): 997-1002

The present invention includes liposomes comprising DHSM having N-acyl or fatty acid chains of any length, including, e.g., 6, 7, 8, 9, 10, 11, 12, 13, 14, 15, 16, 17, 18, 19, 20, 21, 22, 23, or 24 carbon atoms. In certain embodiments, the N-acyl chain consists of 12 to 24 carbon atoms, including 12 or 24 carbon atoms and any integer value within this range. In specific embodiments, the acyl chain consists of 12, 16 or 18 carbon atoms, and in one specific embodiment, it consists of 16 carbon atoms. In another embodiment, it consists of 18 carbon atoms. In another embodiment, the invention includes liposomes having DHSM species having the above chain lengths.

In one embodiment, the invention includes DHSM having matched chain lengths. In naturally occurring SMs, the two chains, i.e., the N-acyl chain and the acyl chain contributed by the sphingosine base, are roughly of equal length (matched) when the N-acyl chain is about 16 carbons long, since the sphingosine acyl chain is mostly of constant length in all molecular species (see above discussion of variations in sphingosine acyl length). Thus, in certain embodiments directed to matched chains DHSM, the N-acyl chain is about 16 carbons long, 16-18 carbons long, or 16 carbons long. In a related embodiment, the N-acyl chain and the sphingosine acyl chain consist of carbon chains not different in length by more than four carbon atoms. In another embodiment, the invention includes liposomes having hydrogenated sphingomyelin having matched chain lengths.

SM isolated from various sources is commercially available (Avanti Polar Lipids, Alabaster, Ala.), and DHSM may be prepared from SM by hydrogenation by any means available in the art. Hydrogenation procedures that may be used according to the invention include, e.g., those described in Kuikka, M. et al., *Biophys. J.* 80:2327-37 (2001) and references cited therein; Barenholz, Y., et al., *Biochemistry* 15(11): 2441-2447 (1976) and references cited therein; and Ollila, F. and Slotte, J. P., *Biochim. Biophys. Acta* 1564:281-288 (2002) and references cited therein. Alternatively, DHSM could be prepared synthetically starting, for example, with dihydrosphingosine, by any means available in the art.

The majority of SMs lack any cis double bonds (see Table 1). Thus, hydrogenation of SM generally targets the trans double bond of the sphingosine base, resulting in DHSM. Of course, hydrogenation of SM would likely also result in hydrogenation of any cis double bonds present in the N-acyl chain. However, it should be understood that according to the present invention, DHSM may comprise one or more cis double bonds in the acyl chain, so long as the trans double bond of the sphingosine base is absent. In one particular embodiment, however, DHSMs of the present invention lack any cis double bonds in the acyl chain and also lack the trans double bond in the sphingosine base.

In certain embodiments of liposomes of the present invention, and the related methods of the present invention, at least 10%, 20%, 30%, 40%, 50%, 60%, 70%, 80%, 90%, 95%, 99%, or 100% (molar basis) of the total phospholipids present in the liposome are DHSM. In one particular embodiment, DHSM comprises at least 50% (molar basis) of the total phospholipids present in the liposome. In another embodiment, DHSM comprises at least 20% (molar basis) of the total phospholipids present in the liposome.

Liposomes comprising DHSM may also further comprise SM that contains the trans double bond in the sphingosine base. Accordingly, in certain embodiments, at least 10%, at least 20%, at least 30%, at least 40%, at least 50%, at least 60%, at least 70%, at least 80%, at least 90%, at least 95%, at least 99%, or 100% (molar basis) of the total SM present in a liposome of the invention is DHSM. In one preferred embodiment, at least 50%, at least 60%, at least 70%, at least 80%, at least 90%, or 100% (molar basis) of the SM present in a liposome of the invention is DHSM.

2. Other Lipids and Liposome Components

Liposomes of the invention may further comprise additional lipids and other components. Other lipids may be included in the liposome compositions of the present invention for a variety of purposes, such as to prevent lipid oxidation or to attach ligands onto the liposome surface. Any of a number of lipids may be present in liposomes of the present invention, including amphipathic, neutral, cationic, and anionic lipids. Such lipids can be used alone or in combination, and can also include bilayer stabilizing components such as polyamide oligomers (see, e.g., U.S. Pat. No. 6,320,017), peptides, proteins, detergents, lipid-derivatives, such as PEG coupled to phosphatidylethanolamine and PEG conjugated to ceramides (see, U.S. Pat. No. 5,885,613).

Any of a number of neutral lipids can be included, referring to any of a number of lipid species that exist either in an uncharged or neutral zwitterionic form at physiological pH, including, e.g., diacylphosphatidylcholine, diacylphosphatidylethanolamine, ceramide, sphingomyelin, cephalin, cholesterol, cerebrosides, diacylglycerols, and sterols.

In certain embodiments, the liposomes of the present invention comprises DHSM and cholesterol. Liposomes comprising SM and cholesterol are referred to as sphingosomes and are described in U.S. Pat. Nos. 5,543,152, 5,741, 516, and 5,814,335. The ratio of DHSM to cholesterol in the liposome composition can vary, but generally is in the range of from about 75/25 (mol/mol) DHSM/cholesterol to about 25/75 (mol/mol) DHSM/cholesterol, more preferably about 60/40 (mol/mol) DHSM/cholesterol to about 40/60 (mol/mol) DHSM/cholesterol, and even more preferably about 55/45 (mol/mol) or 50/50 (mol/mol) DHSM/cholesterol. Generally, if other lipids are included, the inclusion of such lipids will result in a decrease in the DHSM/cholesterol ratio.

In certain embodiments, the liposomes of the present invention comprises DHSM and cholesterol, as well as one or more other phospholipids. The ratio of total phospholipid to cholesterol in the liposome composition can vary, but generally is in the range of from about 75/25 (mol/mol) total phospholipid/cholesterol to about 25/75 (mol/mol) total phospholipid/cholesterol, from about 60/40 (mol/mol) total phospholipid/cholesterol to about 40/60 (mol/mol) total phospholipid/cholesterol, or about 55/45 (mol/mol) or 50/50 (mol/mol) total phospholipid/cholesterol.

Cationic lipids, which carry a net positive charge at about physiological pH, can readily be incorporated into liposomes for use in the present invention. Such lipids include, but are not limited to, N,N-dioleyl-N,N-dimethylammonium chloride ("DODAC"); N-(2,3-dioleyloxy)propyl-N,N-N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

Anionic lipids suitable for use in the present invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In numerous embodiments, amphipathic lipids are included in liposomes of the present invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

In one embodiment, cloaking agents, which reduce elimination of liposomes by the host immune system, can also be included in liposomes of the present invention, such as polyamide-oligomer conjugates, e.g., ATTA-lipids, (see, U.S. Pat. No. 6,320,017) and PEG-lipid conjugates (see, U.S. Pat. Nos. 5,820,873, 5,534,499 and 5,885,613).

Also suitable for inclusion in the present invention are programmable fusion lipid formulations. Such formulations have little tendency to fuse with cell membranes and deliver their payload until a given signal event occurs. This allows the lipid formulation to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the liposome membrane over time. By the time the formulation is suitably distributed in the body, it has lost sufficient cloaking agent so as to be fusogenic. With other signal events, it is desirable to choose a signal that is associated with the disease site or target cell, such as increased temperature at a site of inflammation.

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can comprise the entire protein or fragments thereof.

Targeting mechanisms generally require that the targeting agents be positioned on the surface of the liposome in such a manner that the target moiety is available for interaction with the target, for example, a cell surface receptor. A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002).

The use of liposomes with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). In one approach, a ligand, such as an antibody, for targeting the liposomes is linked to the polar head group of lipids forming the liposome. In another approach, the targeting ligand is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)).

In one embodiment, the liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposomal surface and is configured to correctly position the targeting agent. In some cases, it is possible to attach the target agent directly to the connector portion, but in many instances, it is more suitable to use a third molecule to act as a "molecular bridge." The bridge links the connector portion and the target agent off of the surface of the liposome, thereby making the target agent freely available for interaction with the cellular target.

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci.* (*USA*), 87:2448-2451 (1990). Other examples of antibody conjugation are disclosed in U.S. Pat. No. 6,027,726, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes*, 149 Methods in Enzymology 111-119 (Academic Press, Inc. 1987)). Other targeting methods include the biotin-avidin system.

3. Methods of Preparing Liposomes

A variety of methods for preparing liposomes are known in the art, including e.g., those described in Szoka, et al., *Ann. Rev. Biophys. Bioeng.*, 9:467 (1980); U.S. Pat. Nos. 4,186,183, 4,217,344, 4,235,871, 4,261,975, 4,485,054, 4,501,728, 4,774,085, 4,837,028, 4,946,787; PCT Publication No. WO 91/17424; Deamer and Bangham, *Biochim. Biophys. Acta*, 443:629-634 (1976); Fraley, et al., *Proc. Natl. Acad. Sci. USA*, 76:3348-3352 (1979); Hope, et al., *Biochim. Biophys. Acta*, 812:55-65 (1985); Mayer, et al., *Biochim. Biophys. Acta*, 858:161-168 (1986); Williams, et al., *Proc. Natl. Acad. Sci.*, 85:242-246 (1988); *Liposomes*, Marc J. Ostro, ed., Marcel Dekker, Inc., New York, 1983, Chapter 1; Hope, et al., *Chem. Phys. Lip.*, 40:89 (1986); and Liposomes: A Practical Approach, Torchilin, V. P. et al., ed., Oxford University Press (2003), and references cited therein. Suitable methods include, but are not limited to, sonication, extrusion, high pressure/homogenization, microfluidization, detergent dialysis, calcium-induced fusion of small liposome vesicles, and ether-infusion methods, all of which are well known in the art.

Alternative methods of preparing liposomes are also available. For instance, a method involving detergent dialysis based self-assembly of lipid particles is disclosed and claimed in U.S. Pat. No. 5,976,567, which avoids the time-consuming and difficult to-scale drying and reconstitution steps.

One method produces multilamellar vesicles of heterogeneous sizes (Bangham, A. and Haydon, D. A., *Br Med Bull.* 24(2):124-6 (1968) and Bangham, A. D., *Prog Biophys Mol. Biol.* 18:29-95 (1968)). In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents, such as deoxycholate. Multilamellar vesicles can also be made by dissolving phospholipids in ethanol and then injecting the ethanol solution into a buffer, causing the lipids to spontaneously form liposomes. Further, the trapped volume of the multilamellar vesicles can be increased by a freeze-thaw procedure (Mayer, L D et al., *Biochim. Biophys. Acta*, 817:193-196 (1985)).

Multilamellar vesicles formed on hydration of lipids in buffer are generally heterogeneous in size and contain several concentric lipid bilayers. In many applications, homogeneous liposomes consisting predominantly of only a single bilayer (unilamellar vesicles) and of a size range of about 100 nm to 200 nm are preferred. Several techniques are available for sizing liposomes to a desired size. General methods for sizing liposomes include, e.g., sonication, by bath or by probe, or homogenization, including the method described in U.S. Pat. No. 4,737,323. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10:421-450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve gradual reduction in liposome size. Liposome size can be determined and monitored by known techniques, including, e.g., conventional laser-beam particle size discrimination or the like. Extrusion may be carried out using purpose-built extruders, such as the Lipex Extruder. Defined pore size in the extrusion filters may generate unilamellar liposomal vesicles of specific sizes (Hope M J et al. *Biochim. Biophys. Acta*, 812: 55-65 (1985)). The liposomes may also be formed by extrusion through an asymmetric ceramic filter, such as a Ceraflow Microfilter, commercially available from the Norton Company, Worcester Mass.

Other methods of producing unilamellar vesicles are known. For example, phospholipids can be solubilized into a detergent, e.g., cholates, Triton-X100, or n-alkylglucosides. Following removal of the detergent by any of a number of possible methods including dialysis and gel filtration, liposomes can be formed.

Liposomes of any size may be used according to the present invention. In certain embodiments, liposomes of the present invention have a size ranging from about 0.05 microns to about 0.45 microns, between about 0.05 and about 0.2 microns, or between 0.08 and 0.12 microns in diameter. In one embodiment, liposomes of the present invention are about 0.1 microns in diameter. In other embodiments, liposomes of the present invention are between about 0.45 microns to about 3.0 microns, about 1.0 to about 2.5 microns, about 1.5 to about 2.5 microns and about 2.0 microns.

In certain embodiments, the liposomes used in the present invention comprise a pH gradient across the membrane. In one embodiment, the pH is lower at the interior of the liposomes than at the exterior. Such gradients can be achieved, e.g., by formulating the liposomes in the presence of a buffer with a low pH, e.g., having a pH between about 2 and about 6, and subsequently transferring the liposomes to a higher pH solution. For example, before or after sizing of liposomes, the external pH can be raised, e.g., to about 7 or 7.5, by the addition of a suitable buffer, such as a sodium phosphate buffer. Raising the external pH creates a pH gradient across the liposomal membrane, which promotes efficient drug loading and retention. In one embodiment, the internal pH is between about 3 and 5, and in another embodiment, the internal pH is about 4. Any of a number of buffers can be used, including, e.g., acetate, tartrate, phosphate and citrate buffers.

In numerous embodiments, the liposomes are first formulated in a low pH buffer, and then manipulated in one of a variety of ways to obtain liposomes of the desired size. A pH gradient is then formed by transferring the liposomes into a medium of higher pH or by increasing the pH of the external medium.

In one embodiment, the liposomes used in the present invention comprise a transmembrane potential, while in another embodiment, liposomes of the invention do not comprise a transmembrane potential.

Liposomes prepared according to these methods can be stored for substantial periods of time prior to drug loading and administration to a patient. For example, liposomes can be dehydrated, stored, and subsequently rehydrated and loaded with one or more active agents, prior to administration. Liposomes may also be dehydrated after being loaded with one or more active agents. Dehydration can be accomplished by a variety of methods available in the art, including the dehydration and lyophilization procedures described, e.g., in U.S. Pat. Nos. 4,880,635, 5,578,320, 5,837,279, 5,922,350, 4,857,319, 5,376,380, 5,817,334, 6,355,267, and 6,475,517. In one embodiment, liposomes are dehydrated using standard freeze-drying apparatus, i.e., they are dehydrated under low pressure conditions. Also, the liposomes can be frozen, e.g., in liquid nitrogen, prior to dehydration. Sugars can be added to the liposomal environment, e.g., to the buffer containing the liposomes, prior to dehydration, thereby promoting the integrity of the liposome during dehydration. See, e.g., U.S. Pat. No. 5,077,056 or 5,736,155.

Liposomes may be sterilized by conventional methods at any point during their preparation, including, e.g., after sizing or after generating a pH gradient.

B. Liposomal Compositions Comprising Active Agents

In various embodiments, liposomes of the present invention may be used for many different applications, including the delivery of an active agent to a cell, tissue, organ or subject. For example, liposomes of the invention may be used to deliver a therapeutic agent systemically via the bloodstream or to deliver a cosmetic agent to the skin. Accordingly, liposomal compositions comprising a liposome of the present invention and one or more active agents are included in the present invention.

1. Active Agents

The present invention includes liposomal compositions comprising a liposome of the present invention (i.e., a liposome comprising DHSM) and an active agent. Active agents, as used herein, include any molecule or compound capable of exerting a desired effect on a cell, tissue, organ, or subject. Such effects may be biological, physiological, or cosmetic, for example. Active agents may be any type of molecule or compound, including e.g., nucleic acids, such as single- or double-stranded polynucleotides, plasmids, antisense RNA, RNA interference reagents, including, e.g., DNA-DNA hybrids, DNA-RNA hybrids, RNA-DNA hybrids, RNA-RNA hybrids, short interfering RNAs (siRNA), micro RNAs (mRNA) and short hairpin RNAs (shRNAs); peptides and polypeptides, including, e.g., antibodies, such as, e.g., polyclonal antibodies, monoclonal antibodies, antibody fragments; humanized antibodies, recombinant antibodies, recombinant human antibodies, and Primatized™ antibodies, cytokines, growth factors, apoptotic factors, differentiation-inducing factors, cell surface receptors and their ligands; hormones; and small molecules, including small organic molecules or compounds.

In one embodiment, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative lacks therapeutic activity.

In various embodiments, therapeutic agents include many agents and drugs, such as anti-inflammatory compounds, narcotics, depressants, anti-depressants, stimulants, hallucinogens, analgesics, antibiotics, birth control medication, antipyretics, vasodilators, anti-angiogenics, cytovascular agents, signal transduction inhibitors, vasoconstrictors, hormones, and steroids.

In certain embodiments, the active agent is an oncology drug, which may also be referred to as an anti-tumor drug, an anti-cancer drug, a tumor drug, an antineoplastic agent, or the like. Examples of oncology drugs that may be used according to the invention include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs that may be used according to the invention are ellipticin and ellipticin analogs or derivatives, epothilones, intracellular kinase inhibitors and camptothecins.

In one embodiment, liposomes of the present invention are used to deliver an alkaloid. Accordingly, the invention includes liposomal compositions comprising one or more alkaloids. The present invention includes any naturally occurring alkaloid, including vinca alkaloids, or any synthetic derivative of a naturally occurring alkaloid. Vinca alkaloids include, but are not limited to, vinblastine, vincristine, vindoline, vindesine, vinleurosine, vinrosidine, vinorelbine, or derivatives thereof (see, e.g., the Merck Index, $11^{th}$ Edition (1989) entries 9887, 9891, and 9893, for vinblastine, vincristine, and vindoline).

In another embodiment, liposomes of the present invention are used to deliver podophyllins, podophyllotoxins, and derivatives thereof (e.g., etoposide, etoposide phosphate, teniposide, etc.), camptothecins (e.g., irinotecan, topotecan, etc.), and taxanes (paclitaxol, etc.), and derivatives thereof. All of the above compounds are well known to those of skill and are readily available from commercial sources, by synthesis, or by purification from natural sources.

In certain embodiments, the vinca alkaloid used in the present invention is vincristine. Vincristine, also known as leurocristine sulfate, 22-oxovincaleukoblastine, Kyocristine, vincosid, vincrex, oncovin, Vincasar PFS®, or VCR, is commercially available from any of a number of sources, e.g., Pharmacia & Upjohn, Lilly, IGT, etc. It is often supplied as vincristine sulfate, e.g., as a 1 mg/mL solution.

In other preferred embodiments, the vinca alkaloid used in the present invention is vinorelbine. Vinorelbine includes vinorelbine tartrate. Vinorelbine (5'-noranhydrovinblastine) is a semisynthetic vinca alkaloid structurally distinguished from other members of its class by the modification of the catharanthine nucleus rather than the vindoline ring. Vinorelbine has shown efficacy in NSCLC treatment, alone or in combination with other drugs. Vinorelbine tartrate (Navelbine®) is commercially available from Glaxo Wellcome Inc. (Research Triangle Park, N.C.).

In other preferred embodiments, the vinca alkaloid is vinblastine. Vinblastine is mainly useful for treating Hodgkin's disease, lymphocytic lymphoma, histiocytic lymphoma, advanced testicular cancer, advanced breast cancer, Kaposi's sarcoma, and Letterer-Siwe disease. Vinblastine is given intravenously to treat Kaposi's sarcoma, often in combination with other drugs. Vinblastine (Velban®, Velsar®) is commercially available from Eli Lilly (Indianapolis, Ind.).

In another embodiment, liposomal compositions of the present invention include a taxoid. A taxoid is understood to mean those compounds that include paclitaxels and docetaxel, and other chemicals that have the taxane skeleton (Cortes and Pazdur, 1995). Taxoids may be isolated from natural sources such as the Yew tree or from cultured cells, or taxoids may be chemically synthesized molecules. In one embodiment, a taxoid is a chemical of the general chemical formula, $C_{47}H_{51}NO_{14}$, including [2aR-[2aα,4β,4α,β,6β,9α(αR*,βS*),11α, 12α,12aα,12bα,]]-β-(Benzoylamino)-α-hydroxybenzenepropanoic acid 6, 12b, bis(acetyloxy)-12-(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclodeca [3,4]benz-[1,2-b]oxet-9-yl ester. More recently, a variety of water-soluble taxane prodrugs and salts thereof have been developed, as described, for example, in U.S. Pat. No. 5,981,564, U.S. Patent Publication No. 20020041897, U.S. Pat. No. 6,380,405, and PCT Publication No. WO 02/072010. Other examples of taxane compounds and methods for their preparation are set forth in U.S. Pat. No. 4,942,184. Additional paclitaxel derivatives contemplated for use in the present invention include, for example, the water soluble amino derivatives, including protax-1, described in Mathew et al., *Journal of Medicinal Chemistry* 35, 145-151 (1992) and the taxol prodrugs described in Deutsch et al., *Journal of Medicinal Chemistry,* 32 788-792 (1989), including paclitaxel-C2'-glutaryl-tetramethylene diamine. A variety of other hydrophilic taxane derivatives, including paclitaxel derivatives, have been developed, and the invention contemplates the use of any of these derivatives. Examples of such paclitaxel derivatives include 2'-O-11-amino-3,6,9,12 tetraoxatetradecanoyl paclitaxel, 2'-O-8-amino-3,6-dioxaoctanoyl paclitaxel, and 2'-O-4-aminohexanoyl paclitaxelpaclitaxel-C2'-glutaryl-hexamethylene diamine (taxamine). Further examples include paclitaxel-C2'-glutaryl-di-(glucosamine), and paclitaxel-C2'C7-di-(glutaryl-di-glucosamine).

In one embodiment, the invention includes liposomal compositions comprising a camptothecin. Camptothecin (CPT) compounds include various 20(S)-camptothecins, analogs of 20(S)camptothecin, and derivatives of 20(S)-camptothecin. Camptothecin, when used in the context of this invention, includes the plant alkaloid 20(S)-camptothecin, both substituted and unsubstituted camptothecins, and analogs thereof. Examples of camptothecin derivatives include, but are not limited to, 9-nitro-20(S)-camptothecin, 9-amino-20(S)-camptothecin, 9-methyl-camptothecin, 9-chlorocamptothecin, 9-flouro-camptothecin, 7-ethyl camptothecin, 10-methylcamptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10,11-methylenedioxy camptothecin. Prodrugs of camptothecin include, but are not limited to, esterified camptothecin derivatives as described in U.S. Pat. No. 5,731,316, such as camptothecin 20-O-propionate, camptothecin 20-O-butyrate, camptothecin 20-O-valerate, camptothecin 20-O-heptanoate, camptothecin 20-O-nonanoate, camptothecin 20-O-crotonate, camptothecin 20-O-2',3'-epoxy-butyrate, nitrocamptothecin 20-O-acetate, nitrocamptothecin 20-O-propionate, and nitrocamptothecin 20-O-butyrate. Particular examples of 20(S)-camptothecins include 9-nitrocamptothecin, 9-aminocamptothecin, 10,11-methylendioxy-20(S)camptothecin, topotecan, irinotecan, SN-38, 7-ethyl-10-hydroxy camptothecin, or another substituted camptothecin that is substituted at least one of the 7, 9, 10, 11, or 12 positions.

Camptothecins may optionally be substituted. Substitutions may be made to the camptothecin scaffold, while still retaining activity. In certain embodiments, the camptothecin scaffold is substituted at the 7, 9, 10, 11, and/or 12 positions. Such substitutions may serve to provide differential activities over the unsubstituted camptothecin compound. Examples of substituted camptothecins include 9-nitrocamptothecin, 9-aminocamptothecin, 10,11-methylendioxy20(S)-camptothecin, topotecan, irinotecan, 7-ethyl-10-hydroxy camptothecin, or another substituted camptothecin that is substituted at least one of the 7, 9, 10, 11, or 12 positions.

Native, unsubstituted, camptothecin can be obtained by purification of the natural extract, or may be obtained from the Stehlin Foundation for Cancer Research (Houston, Tex.). Substituted camptothecins can be obtained using methods known in the literature, or can be obtained from commercial suppliers. For example, 9-nitrocamptothecin may be obtained from SuperGen, Inc. (San Ramon, Calif.), and 9-aminocamptothecin may be obtained from Idec Pharmaceuticals (San Diego, Calif.). Camptothecin and various analogs may also be obtained from standard fine chemical supply houses, such as Sigma Chemicals.

In an additional embodiment, the invention includes liposomal compositions comprising etoposide. Etoposide (also referred to as VP-16, VP-16-213, or VePesid®), a semi-synthetic podophyllotoxin derived from the root of *Podophyllum peltatum* (mandrake plant), is a widely used cancer chemotherapy drug that is approved for clinical use in non-Hodgkin's lymphoma, small cell lung cancer, and refractory testicular cancer. In another embodiment, the liposomal composition of the invention comprises the etoposide derivative, NK611, or a pharmaceutically acceptable salt thereof.

While liposomal compositions of the invention generally comprise a single active agent, in certain embodiments, they may comprise more than one active agent.

2. Methods of Loading Liposomes

Liposomal formulations of the invention are generally prepared by loading an active agent into liposomes. Loading may be accomplished by any means available in the art, including those described in further detail below. Furthermore, the invention contemplates the use of either passive or active loading methods.

Passive loading generally requires addition of the drug to the buffer at the time the liposomes are formed or reconstituted. This allows the drug to be trapped within the liposome interior, where it will remain if it is not lipid soluble and if the vesicle remains intact (such methods are described, e.g., in PCT Publication No. WO 95/08986). The buffer which is used in the formation of the liposomes can be any biologically compatible buffer solution of, for example, isotonic saline, phosphate buffered saline, dextrose solutions (e.g., 5% dextrose) or other low ionic strength buffers. The resulting liposomes encompassing the active agent can then be sized as described above.

In the case of hydrophobic drugs, the drug and liposome components can be dissolved in an organic solvent in which all species are miscible and concentrated to a dry film. A buffer is then added to the dried film and liposomes are formed having the drug incorporated into the lipid bilayer. The liposomes containing the bilayer-inserted drug can then be sized as described above.

Liposomal compositions of the invention may also be prepared using active loading methods. Numerous methods of active loading are known to those of skill in the art. Such methods typically involve the establishment of some form of gradient that draws lipophilic compounds into the interior of liposomes where they can reside for as long as the gradient is maintained. Very high quantities of the desired active agent can be obtained in the interior. At times, the active agent may precipitate out in the interior. A wide variety of active agents can be loaded into liposomes with encapsulation efficiencies approaching 100% by using active loading methods involving a transmembrane pH or ion gradient (see, Mayer, et al., *Biochim. Biophys. Acta* 1025:143-151 (1990) and Madden, et al., *Chem. Phys. Lipids* 53:37-46 (1990)).

Transmembrane potential loading has been described in detail in U.S. Pat. Nos. 4,885,172; 5,059,421; 5,171,578; and 5,837,282 (which teaches ionophore loading). Briefly, the transmembrane potential loading method can be used with essentially any active agent, including, e.g., conventional drugs, that can exist in a charged state when dissolved in an appropriate aqueous medium. In certain embodiments, the active agent will be relatively lipophilic facilitating diffusion across the lipid bilayer. A transmembrane potential is created across the bilayers of the liposomes or protein-liposome complexes and the active agent is loaded into the liposome by means of the transmembrane potential. The transmembrane potential is generated by creating a concentration gradient for one or more charged species (e.g., $Na^+$, $K^+$, and/or $H^+$) across the membranes. This concentration gradient is generated by producing liposomes having different internal and external media and has an associated proton gradient. Active agent accumulation can then occur in a manner predicted by the Henderson-Hasselbach equation.

One particular method of loading active agents, including, e.g., vinca alkaloids, to produce a liposomal composition of the present invention is ionophore-mediated loading, as disclosed and claimed in U.S. Pat. No. 5,837,282. One example of an ionophore used in this procedure is A23187. Liposomes can be formed including a divalent cation, such as magnesium or manganese, in the aqueous interior. External divalent cation is then removed creating a chemical gradient across the liposomal bilayer. Addition of A23187 to the liposomes facilitates transfer of divalent cation out of the liposomes and hydrogen ion transport into the liposomes in a 1:2 ratio (i.e., no net charge transfer). As ionophore-mediated loading is an electroneutral process, there is no transmembrane potential generated.

Accordingly, the invention provides methods of loading liposomes via ionophore-mediated loading. Similarly, the invention provides methods of preparing or manufacturing a liposomal composition of the invention comprising loading a liposome comprising DHSM with a therapeutic agent according to the method of loading liposomes described here, including ionophore-mediated loading. The invention also provides any of the liposomes described herein comprising a divalent cation, such as $Mn^{2+}$ or $Mg^{2+}$ in their interior.

While ionophore-mediated loading methods have been generally described in U.S. Pat. No. 5,837,282, it was surprisingly discovered that increased drug encapsulation is achieved by using certain specific conditions within the general ranges previously disclosed. As shown in Table 2, increased encapsulation is achieved using either the divalent metal ion, $Mn^{2+}$, increased salt concentration, higher loading temperatures, or a combination of such conditions.

TABLE 2

Percent NK611 encapsulation via ionophore-mediated loading

| D/L ratio | Buffer | Temp (° C.) | SM/Chol (% encap.) | DHSM/Chol (% encap.) |
|---|---|---|---|---|
| 0.4 | 300 mM MgSO$_4$ | 60 | 78 | 14 |
| 0.4 | 300 mM MnSO$_4$ | 60 | 88-93 | 74-83 |
| 0.4 | 300 mM MnSO$_4$ | 70 | n.d.[1] | 82-93 |
| 1.0 | 300 mM MgSO$_4$ | 60 | 45 | n.d. |
| 1.0 | 300 mM MnSO$_4$ | 60 | 53 | n.d. |
| 1.0 | 600 mM MnSO$_4$ | 70 | n.d. | 79-90 |

[1]n.d. indicates not determined

Thus, the present invention includes methods of loading an active agent (e.g., a therapeutic agent) into a liposome, wherein the liposome has an encapsulated medium comprising MnSO$_4$, by incubating said liposomes with an external solution comprising the active agent and an ionophore. Thus, in one preferred embodiment, the divalent metal ion is $Mn^{2+}$, and in certain preferred embodiments, the MnSO$_4$ is present at a concentration equal or greater than 300 mM or in the range from 300 mM to 600 mM. In particular preferred embodiments, the MnSO$_4$ is present at a concentration of either 300 mM or 600 mM.

In additional embodiments, the loading is performed at a temperature of at least 60° C., at least 65° C., or at least 70° C. In particular embodiments, loading is performed at a temperature in the range of 60° to 70°, and in certain embodiments, loading is performed at either 60° C. or 70° C. Loading may be performed in the presence of any concentration of active agent (e.g., drug), or at any desired drug to lipid ratio, including any of the drug to lipid ratios described herein. In certain embodiments, loading is performed at a drug to lipid ratio within the range of 0.005 drug:lipid (by weight) to about 1.0 drug:lipid (by weight). In particular embodiments, loading is performed at a drug to lipid ratio within the range of 0.075 drug:lipid (by weight) to 0.20 drug:lipid (by weight). In other particular embodiments, loading is performed at a drug to lipid ratio of between 0.2 drug:lipid (by weight) to 0.4 drug:lipid (by weight). In other particular embodiments, loading is performed at between 0.4 drug:lipid (by weight) and 1.0 drug:lipid (by weight).

In additional specific embodiments, the preferred loading methods are used to load liposomes of the invention, i.e., liposomes comprising DHSM, wherein at least 50% of the total phospholipids present in the liposomes are DHSM. Thus, in one particular embodiment, the invention includes a method of ionophore-mediated loading of a therapeutic agent into a liposome comprising DHSM, wherein said DHSM comprises at least 50% of the total phospholipids of the liposome and wherein said liposomes have an encapsulated medium comprising 300 mM $MnSO_4$, comprising incubating said liposomes with an external solution comprising said therapeutic agent and an ionophore at a temperature of 70° C. to form therapeutic agent-loaded liposomes.

The present invention also provides methods of preparing liposomal compositions and methods of making or manufacturing liposomal compositions of the present invention. In general, such methods comprise loading a liposome of the present invention with an active agent. Loading may be accomplished by any means available in the art, including those described herein, and, particularly, ionophore-mediated loading methods described here. Such methods may further comprise formulating the resulting composition to produce a pharmaceutical composition suitable for administration to a subject.

In one embodiment, a method of the invention comprises loading a liposome comprising DHSM with a therapeutic agent. In a related embodiment, a method of the invention comprises producing a liposome comprising DHSM or and loading the liposome with a therapeutic agent. In specific embodiments, the liposomes have additional components or characteristics as described in the instant application.

3. Characteristics of Liposomal Compositions

Liposomal compositions of the present invention may be characterized in a variety of ways, based, in part, upon their lipid and active agent components.

One important characteristic of liposomal compositions used for pharmaceutical purposes is the drug:lipid ratio. The rate of drug release from the liposomes may be decreased by increasing the drug:lipid ratio and thereby causing precipitation of a proportion of the encapsulated drug (see U.S. Patent Publication No. 2002/0119990-A1). As the drug:lipid ratio is increased however, lower lipid doses are administered to a patient to achieve the desired drug dose. This may result in faster clearance of the drug-loaded liposomes from the plasma and hence reduce drug delivery to disease sites, including tumor sites. Addition of empty liposomes (liposomes containing no drug) to drug-loaded liposomes can allow administration of a suitable lipid dose to prevent rapid clearance from the plasma while maintaining slow drug release from the drug-loaded liposomes (see U.S. Patent Publication No. 2002/0119990-A1). Techniques for generating specific drug:lipid ratios are well known in the art. The drug:lipid ratio can be varied by using appropriate concentrations of drug and liposomes during the drug loading procedure, as described, for example, in Mayer et al., Cancer Res. 49: 5922-5930 (1989).

In the present invention, it is envisaged that for different applications, different drug:lipid ratios may be desired. Drug:lipid ratios can be measured on a weight to weight basis, a mole to mole basis or any other designated basis.

In certain embodiments, drug:lipid ratios range from 0.005 drug:lipid (by weight) to about 1.0 drug:lipid (by weight). In other embodiments, drug:lipid ratios range from 0.075 drug:lipid (by weight) to 0.20 drug:lipid (by weight). In other particular embodiments, drug:lipid ratios range from between 0.2 drug:lipid (by weight) to 0.4 drug:lipid (by weight). In other particular embodiments, drug:lipid ratios range between 0.4 drug:lipid (by weight) and 1.0 drug:lipid (by weight). In particular embodiments, the drug:lipid ratio is approximately 0.05 (by weight) when the drug is vincristine, approximately 0.3 (by weight) when the drug is vinorelbine, approximately 0.1 (by weight) when the drug is topotecan, approximately 0.4 (by weight) when the drug is NK611, and approximately 0.1 (by weight) when the drug is taxol.

In certain embodiments, liposomal compositions of the present invention comprise both empty liposomes and liposomes loaded with one or more active agents. In a particular embodiment, a liposomal composition of the present invention comprises empty liposomes, and liposomes loaded with one or more active agents, wherein the loaded liposomes comprise DHSM and an internal buffer comprising $MnSO_4$ or $Mn^{2+}$.

Liposomal compositions used for pharmaceutical purposes are often intended to modify drug biodistribution, drug half-life in plasma, drug stability in plasma, or duration of drug exposure to target cells (e.g., tumor cells). Ultimately such changes in drug pharmacokinetics are expected to result in increased drug activity, for example, increased antitumor activity. Characterization of the liposomal compositions of the present invention therefore appropriately includes pharmacokinetics evaluation, determination of drug release from the liposomes in vitro and/or in vivo, and determination of the therapeutic activity of the liposomal drug. Accordingly, in various embodiments, liposomes and liposomal compositions of the present invention retain at least 10%, at least 15%, at least 20%, at least 30%, at least 40%, at least 50%, at least 60%, at least 70%, at least 80%, or at least 90% of active compound at one hour, as determined by the in vitro release (IVR) method described in Example 5. In other embodiments, liposomes and liposomal compositions of the present invention retain at least 20%, at least 30%, at least 40%, at least 50%, at least 60%, at least 70%, at least 80%, or at least 90% of active compound at four, eight or twenty-four hours, as determined by the IVR method described in Example 5. Similarly, in certain embodiments, liposomes and liposomal compositions of the present invention are associated with active agent plasma retention of at least 10%, at least 15%, at least 20%, at least 30%, at least 40%, at least 50%, at least 60%, at least 70%, at least 80%, or at least 90% four hours post injection or at least 10%, at least 15%, at least 20%, at least 30%, at least 40%, at least 50%, at least 60%, at least 70%, at least 80%, or at least 90% eight or twenty-four hours post injection, as measured in an in vivo model, such as that described in Examples 6-8.

In other embodiments of the invention, the liposomes or liposomal compositions of the invention have a plasma circulation half-life of at least 0.5, 0.8, 1.2, 1.5, 2.0, 4.0, 6.0, 8.0, or 12 hours. In other embodiments, liposomal compositions of the present invention have a plasma drug half-life of at least 0.5, 0.8, 1.2, 1.5, 2.0, 4.0, 6.0, 8.0, or 12 hours. Circulation and blood or plasma clearance half-lives may be determined as described, for example, in U.S. Patent Publication No. 2004-0071768-A1.

In related embodiments, the circulation half-life of encapsulated vinorelbine in blood is at least 0.8 hours, or the time required for 50% release of encapsulated vinorelbine from the liposomes in blood is at least 2.0 hours.

In related embodiments, the circulation half-life of encapsulated topotecan in blood is at least 1.0 hour, or the time required for 50% release for encapsulated topotecan from the liposomes in blood is at least 2.0 hours.

As described herein, it was a surprising finding of the present invention that liposomal compositions comprising DHSM or $Mn^{2+}$ as the internal cation exhibit increased drug retention as compared to liposomal compositions comprising ESM or $Mg^{2+}$. In certain embodiments, therefore, the present invention provides liposomal compositions comprising an active agent and $MnSO_4$ or $Mn^{2+}$ in the interior of the liposomes. In a related embodiment, the salt or divalent cation in the interior of liposomes comprising an active agent is $MnSO_4$ or $Mn^{2+}$. In one embodiment, the active agent is topotecan, and the present invention includes a liposomal composition comprising topotecan and $MnSO_4$ or $Mn^{2+}$ in the interior of the liposomes. Furthermore, it was a surprising finding of the present invention that $Mn^{2+}$ and DHSM exhibited an additive effective in increasing drug retention. Accordingly, in one particular embodiment, liposomal compositions of the present invention comprise both DHSM and $Mn^{2+}$. Such liposomes may further comprise a therapeutic agent, such as, e.g., topotecan. Liposomal compositions comprising $MnSO_4$ or $Mn^{2+}$ can be prepared essentially as known in the art, and as described herein, e.g., by substituting $MnSO_4$ for other salts, such as $MgSO_4$.

The present invention also provides liposomes and liposomal compositions in kit form. The kit may comprise a ready-made formulation or a formulation that requires mixing before administration. The kit will typically comprise a container that is compartmentalized for holding the various elements of the kit. The kit will contain the liposomes or liposomal compositions of the present invention or the components thereof, in hydrated or dehydrated form, with instructions for their rehydration and administration. In particular embodiments, a kit comprises at least one compartment containing a liposome of the present invention that is loaded with an active agent. In another embodiment, a kit comprises at least two compartments, one containing a liposome of the invention and the other containing an active agent. Of course, it is understood that any of these kits may comprise additional compartments, e.g., a compartment comprising a buffer, such as those described in U.S. Patent Publication No. 2004-0228909-A1. Kits of the present invention, which comprise liposomes comprising DHSM, may also contain other features of the kits described in U.S. Patent Publication No. 2004-0228909 A1. Further the kit may contain drug-loaded liposomes in one compartment and empty liposomes in a second compartment. Alternatively, the kit may contain a liposome of the present invention, an active agent to be loaded into the liposome of the present invention in a second compartment, and an empty liposome in a third compartment.

In a particular embodiment, a kit of the present invention comprises a therapeutic compound encapsulated in a liposome comprising DHSM, wherein said DHSM constitutes at least 20% or at least 50% (molar basis) of total phospholipids present in the liposome, as well as an empty liposome. In one embodiment, the liposome containing therapeutic compound and the empty liposome are present in different compartments of the kit.

C. Liposomal Delivery of Active Agents

The liposomal compositions described above may be used for a variety of purposes, including the delivery of an active agent or therapeutic agent or compound to a subject or patient in need thereof. Subjects include both humans and non-humans animals. In certain embodiments, subjects are mammals. In other embodiments, subjects are one or more particular species or breed, including, e.g., humans, mice, rats, dogs, cats, cows, pigs, sheep, or birds.

Thus, the present invention also provides methods of treatment for a variety of diseases and disorders, as well as methods related to cosmetic purposes, including, but not limited to, methods of applying cosmetics and methods of providing cosmetics, makeup products, moisturizers or other compounds, including, e.g., those intended to provide a cosmetic benefit.

1. Methods of Treatment

The liposomal compositions of the present invention may be used to treat any of a wide variety of diseases or disorders, including, but not limited to, inflammatory diseases, cardiovascular diseases, nervous system diseases, tumors, demyelinating diseases, digestive system diseases, endocrine system diseases, reproductive system diseases, hemic and lymphatic diseases, immunological diseases, mental disorders, muscoloskeletal diseases, neurological diseases, neuromuscular diseases, metabolic diseases, sexually transmitted diseases, skin and connective tissue diseases, urological diseases, and infections.

In one embodiment, the liposomal compositions and methods described herein can be used to treat any type of cancer. In particular, these methods can be applied to cancers of the blood and lymphatic systems, including lymphomas, leukemia, and myelomas. Examples of specific cancers that may be treated according to the invention include, but are not limited to, Hodgkin's and non-Hodgkin's Lymphoma (NHL), including any type of NHL as defined according to any of the various classification systems such as the Working formulation, the Rappaport classification and, preferably, the REAL classification. Such lymphomas include, but are not limited to, low-grade, intermediate-grade, and high-grade lymphomas, as well as both B-cell and T-cell lymphomas. Included in these categories are the various types of small cell, large cell, cleaved cell, lymphocytic, follicular, diffuse, Burkitt's, Mantle cell, NK cell, CNS, AIDS-related, lymphoblastic, adult lymphoblastic, indolent, aggressive, transformed and other types of lymphomas. The methods of the present invention can be used for adult or childhood forms of lymphoma, as well as lymphomas at any stage, e.g., stage I, II, III, or IV. The various types of lymphomas are well known to those of skill, and are described, e.g., by the American Cancer Society (see, e.g., www3.cancer.org).

The compositions and methods described herein may also be applied to any form of leukemia, including adult and childhood forms of the disease. For example, any acute, chronic, myelogenous, and lymphocytic form of the disease can be treated using the methods of the present invention. In preferred embodiments, the methods are used to treat Acute Lymphocytic Leukemia (ALL). More information about the various types of leukemia can be found, inter alia, from the Leukemia Society of America (see, e.g., www.leukemia.org).

Additional types of tumors can also be treated using the methods described herein, such as neuroblastomas, myelomas, prostate cancers, small cell lung cancer, colon cancer, ovarian cancer, non-small cell lung cancer, brain tumors, breast cancer, and others.

The liposomal compositions of the invention may be administered as first line treatments or as secondary treatments. In addition, they may be administered as a primary chemotherapeutic treatment or as adjuvant or neoadjuvant chemotherapy. For example, treatments of relapsed, indolent, transformed, and aggressive forms of non-Hodgkin's Lymphoma may be administered following at least one course of a primary anti-cancer treatment, such as chemotherapy and/or radiation therapy.

2. Administration of Liposomal Compositions

Liposomal compositions of the invention are administered in any of a number of ways, including parenteral, intravenous, systemic, local, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection. For example, in one embodiment, a patient is given an intravenous infusion of the liposome-encapsulated active agent through a running intravenous line over, e.g., 5-10 minutes, 15-20 minutes, 30 minutes, 60 minutes, 90 minutes, or longer. In one embodiment, a 60 minute infusion is used. In other embodiments, an infusion ranging from 6-10 or 15-20 minutes is used. Such infusions can be given periodically, e.g., once every 1, 3, 5, 7, 10, 14, 21, or 28 days or longer, preferably once every 7-21 days, and preferably once every 7 or 14 days.

Liposomal compositions of the invention may be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The concentration of drug and liposomes in the pharmaceutical formulations can vary widely, i.e., from less than about 0.05%, usually at or at least about 2-5% to as much as 10 to 30% by weight and will be selected depend upon the particular drug used, the disease state being treated and the judgment of the clinician taking. Further, the concentration of drug and liposomes will also take into consideration the fluid volume administered, the osmolality of the administered solution, and the tolerability of the drug and liposomes. In some instances it may be preferable to use a lower drug or liposome concentration to reduce the incidence or severity of infusion-related side effects.

Suitable formulations for use in the present invention can be found, e.g., in *Remington's Pharmaceutical Sciences*, Mack Publishing Company, Philadelphia, Pa., 17$^{th}$ Ed. (1985). Often, intravenous compositions will comprise a solution of the liposomes suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) or 5% dextrose will be used. These compositions can be sterilized by conventional sterilization techniques, such as filtration. The resulting aqueous solutions may be packaged for use or filtered under aseptic conditions and lyophilized, the lyophilized preparation being combined with a sterile aqueous solution prior to administration. The compositions may also contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the composition may include lipid-protective agents, which protect lipids against free-radical and lipid-peroxidative damages on storage. Lipophilic free-radical quenchers, such as α-tocopherol and water-soluble iron-specific chelators, such as ferrioxamine, are suitable.

The amount of active agent administered per dose is selected to be above the minimal therapeutic dose but below a toxic dose. The choice of amount per dose will depend on a number of factors, such as the medical history of the patient, the use of other therapies, and the nature of the disease. In addition, the amount of active agent administered may be adjusted throughout treatment, depending on the patient's response to treatment and the presence or severity of any treatment-associated side effects. In certain embodiments, the dosage of liposomal composition or the frequency of administration is approximately the same as the dosage and schedule of treatment with the corresponding free active agent. However, it is understood that the dosage may be higher or more frequently administered as compared to free drug treatment, particularly where the liposomal composition exhibits reduced toxicity. It is also understood that the dosage may be lower or less frequently administered as compared to free drug treatment, particularly where the liposomal composition exhibits increased efficacy as compared to the free drug. Exemplary dosages and treatment for a variety of chemotherapy compounds (free drug) are known and available to those skilled in the art and are described in, e.g., *Physician's Cancer Chemotherapy Drug Manual*, E. Chu and V. Devita (Jones and Bartlett, 2002).

Patients typically will receive at least two courses of such treatment, and potentially more, depending on the response of the patient to the treatment. In single agent regimens, total courses of treatment are determined by the patient and physician based on observed responses and toxicity.

3. Combination Therapies

In numerous embodiments, liposomal compositions of the invention will be administered in combination with one or more additional compounds or therapies, such as surgery, radiation treatment, chemotherapy, or other active agents, including any of those described above. Liposomal compositions may be administered in combination with a second active agent for a variety of reasons, including increased efficacy or to reduce undesirable side effects. The liposomal composition may be administered prior to, subsequent to, or simultaneously with the additional treatment. Furthermore, where a liposomal composition of the present invention (which comprises a first active agent) is administered in combination with a second active agent, the second active agent may be administered as a free drug, as an independent liposomal formulation, or as a component of the liposomal composition comprising the first drug. In certain embodiments, multiple active agents are loaded into the same liposomes. In other embodiments, liposomes comprising an active agent are used in combination with one or more free drugs. In particular embodiments, liposomal compositions comprising an active agent are formed individually and subsequently combined with other compounds for a single co-administration. Alternatively, certain therapies are administered sequentially in a predetermined order, such as in CHOP or lipo-CHOP, described further below. Accordingly, liposomal compositions of the present invention may comprise one or more active agents.

In one embodiment of combination treatment according to the present invention, multiple vinca alkaloids are co-administered, or one or more vinca alkaloids is administered in conjunction with another therapeutic compound, such as cyclophosphamide, dexamethasone, doxorubicin, prednisone, other antineoplastics such as the taxanes, camptothecins, and/or podophyllins, other chemotherapeutic agents such as antisense drugs or anti-tumor vaccines. In one embodiment, liposome encapsulated vincristine is used along with cyclophosphamide, doxorubicin, and prednisone, thereby forming an improved CHOP formulation comprising liposome encapsulated vincristine ("lipo-CHOP"). In a related embodiment, lipo-CHOP is used in combination with one or more additional therapeutic compounds, such as Rituxan™ (IDEC Pharmaceuticals). In another embodiment, liposome encapsulated vincristine is used in combination with prednisone.

In other embodiments, liposomal vinorelbine is used in combination with one or more other chemotherapeutic agents, such as Gemcitabine or taxol or derivatives thereof. Combination therapies including vinorelbine have been demonstrated to have increased efficacy as compared to single drug treatment, in certain cases. For example, vinorelbine is associated with promising six-month and median survival rates in women with ovarian cancer that has relapsed following treatment with a platinum and paclitaxel, and the combination of vinorelbine and cisplatin has shown superior results in terms of response rates and survival when compared to single-agent cisplatin. Wozniak, A. J. et al., *J. Clin. Oncol.* 16:2459-2465 (1998).

Liposomal compositions of the invention, including, e.g., liposome-encapsulated vinca alkaloids, can also be combined with anti-tumor agents such as monoclonal antibodies including, but not limited to, Oncolym™ (Techniclone Corp. Tustin, Calif.) or Rituxan™ (IDEC Pharmaceuticals), Bexxar™ (Coulter Pharmaceuticals, Palo Alto, Calif.), IDEC-Y2B8 (IDEC Pharmaceuticals Corporation), Erbitux™ (Imclone Systems Inc.) and Avastin™ (Genentech Corp.).

In a preferred embodiment, liposomal compositions of the present invention are administered in combination with an anti-cancer compound or therapy that provides an increased or synergistic improvement in tumor reduction based on mechanism of action and non-overlapping toxicity profiles. For example, liposomal vinca alkaloids can be delivered with a taxane, which optionally may also be a liposomal taxane. While it is thought that vinca alkaloids depolymerize microtubules and taxanes stabilize microtubules, the two compounds have been found to act synergistically in the impairment of tumor growth, presumably because both are involved in the inhibition of microtubule dynamics. See, Dumontet, C. and Sikic, B. I. (1999) *J. Clin Onc.* 17(3) 1061-1070. Liposomal formulations of the vinca alkaloids according to the present invention will thus significantly diminish the myeloid and neurologic toxicity associated with the sequential administration of free form vinca alkaloids and taxanes.

Other combination therapies known to those of skill in the art can be used in conjunction with the methods of the present invention.

Examples of drugs used in combination with conjugates and other chemotherapeutic agents to combat undesirable side effects of cancer or chemotherapy include zoledronic acid (Zometa) for prevention of bone metastasis and treatment of high calcium levels, Peg-Filgrastim for treatment of low white blood count, SDZ PSC 833 to inhibit multidrug resistance, and NESP for treatment of anemia.

EXAMPLE 1

Preparation of Liposomes Comprising Dihydrosphingomyelin

Dihydrosphingomyelin can be prepared by hydrogenation of sphingomyelin. By way of example, details are provided below for preparation of egg dihydrosphingomyelin (EDHSM) and D-erythro-N-palmitoyl-dihydrosphingomyelin (16:0-DHSM).

Egg Dihydrosphingomyelin.

Essentially, egg sphingomyelin (ESM) (25 g) was dissolved in ethanol (250 mL) in a round-bottomed flask. 10% palladium/carbon catalyst (2.5 g) was added, and the flask was sealed with a rubber septum. The flask was flushed with argon for 30 minutes. Hydrogen was slowly passed through the system, using a bubbler to prevent flowback of air into the reaction mixture. The reaction was warmed in a water bath at approximately 40° C. on a stirrer for approximately two hours and then flushed with argon to remove excess hydrogen. Cyclohexene (5 mL) was added to quench any active catalyst remaining. The suspension was filtered through diatomaceous earth, observing the proper precautions when filtering pyrophoric solids. The filtrate was dried down on a rotovap, and the residue dissolved in warmed ethanol (100 mL). The solution was cooled and acetone (100 mL) added. The solution was cooled to room temperature, and the resultant precipitate filtered off under vacuum. The precipitation was repeated, and the resultant product dried under vacuum, yielding 14 g of purified dihydrosphingomyelin (DHSM).

DHSM prepared according to the above procedure was analyzed by nuclear magnetic resonance (NMR) and high pressure liquid chromatography (HPLC). NMR spectra analysis of two batches of DHSM prepared from egg sphingomyelin indicated that less than 1% of the double bonds present in the egg sphingomyelin starting material were still present in the prepared DHSM. HPLC analysis of two batches of DHSM prepared from egg sphingomylein and one batch of DHSM prepared from brain sphingomyelin demonstrated that greater than 97% of the prepared DHSM possessed a 16:0, 18:0, 20:0, 22:0, 23:0 or 24:0 N-acyl chain. Conversion of sphingosine to dihydrosphingosine was efficient with only about 0.5-1.0% of the starting material present in the final product (based on D-erythro-N-palmityl-sphingomyelin).

D-erythro-N-palmityl-dihydrosphingomyelin (16:0-DHSM)

To prepare 16:0-DHSM, D-erythro-N-palmityl-sphingomyelin (16:0-SM) was purified from egg yolk sphingomyelin (Avanti Polar Lipids, Inc. (Alabaster, Ala.) by reverse-phase HPLC (LiChrospher 100 RP-18 columns, 5 μm particle size, 240×4 mm column dimensions; Merck, Darmstadt, Germany) using 5 vol-% water in methanol as eluent (at 1 ml/min, column temperature 40° C.). D-erythro-N-palmityl-dihydrosphingomyelin (16:0-DHSM) was prepared from 16:0-SM by hydrogenation using palladium oxide (Aldrich Chemical Co., Milwaukee, Wis.), as catalyst (Schneider and Kennedy, J. Lipid Res. 8:202-209 (1967)), and purified as described for egg dihydrosphingomyelin.

Liposomes comprising sphingomyelin derived from various sources or dihydrosphingomyelin (DHSM) were generated according to standard procedures. Liposomes comprising SM or DHSM were prepared essentially as previously described in Fenske, D. B. et al., *Biochim Biophys Acta.* 1414(1-2):188-204 (1998) and Webb, M. S. et al., *Br J Can-* cer 72(4):896-904 (1995), using ethanol as described in Boman, N. L. et al., *Cancer Res.* 54(11):2830-3 (1994).

EXAMPLE 2

Differential Scanning Calorimetry (DSC) of Liposomes Comprising Dihydrosphingomyelin The thermotropic properties of various dihydrosphingomyelins and the corresponding sphingomyelins were characterized using differential scanning calorimetry. Large multilamellar liposomes composed of the various DHSM and SM species were prepared in distilled water at a phospholipid concentration of 15 mg/mL. Before loading in DSC cells, samples were brought to room temperature and then degassed under vacuum with stirring for 5 minutes. Immediately prior to loading in DSC cells, samples were vortexed to achieve homogeneity. Scans were performed on a MC-DSC 4100 calorimeter from Calorimetry Sciences Corporation, using a heating or cooling rate of 5° C./hour. Generally both heating and cooling scans were performed over the temperature range 20-60° C.

Concentration-normalized DSC scans for ESM and EDHSM are shown in FIG. 1. The scans show a gel to liquid-crystalline phase transition for both liposomal compositions. The transition temperature (Tc) for ESM is approximately 34° C., while the Tc for EDHSM is approximately 46° C. A narrow, single transition is seen for EDHSM and a distinct pre-transition is seen at about 38° C.

Figure 2:
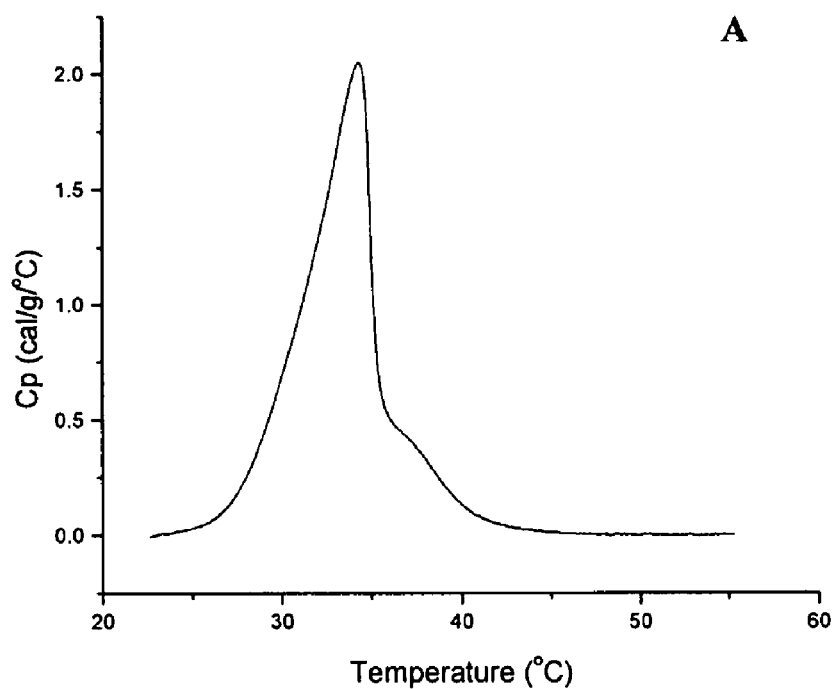
FIG. 2 depicts concentration-normalized DSC data for milk sphingomyelin (MSM) (A) or milk dihydrosphingomyelin (MDHSM) (B). Samples were scanned from 20 to 60° C. at a scan rate of 5° C./hr.
Figure 2:
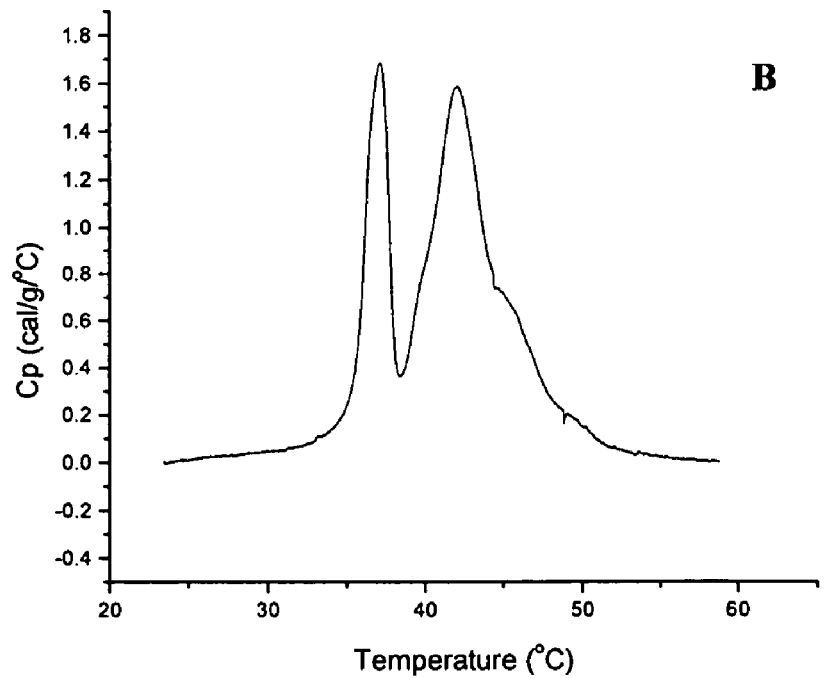

Concentration-normalized DSC scans for milk sphingomyelin (MSM) and milk dihydrosphingomyelin (MDHSM) are shown in FIG. 2. The scans show a gel to liquid-crystalline phase transition for both liposomal compositions. The phase transition for MSM is broad with a Tc of approximately 26° C. In the case of MDHSM, two distinct transitions are seen with the first Tc being about 34° C. The presence of two endotherms suggests that phase separation may occur in liposomes composed of MDHSM when these are cooled below the Tc. It is noted that the N-acyl chains in MDHSM are predominantly C22:0, C23:0 and C24:0 with relatively small quantities of C16:0 or C18:0 present (Table 1). Without wishing to be bound by any particular theory, the difference in chain length between the dihydrosphingosine long chain base and the N-acyl chains may contribute to the complex thermotropic behavior observed with MDHSM.

Figure 3:
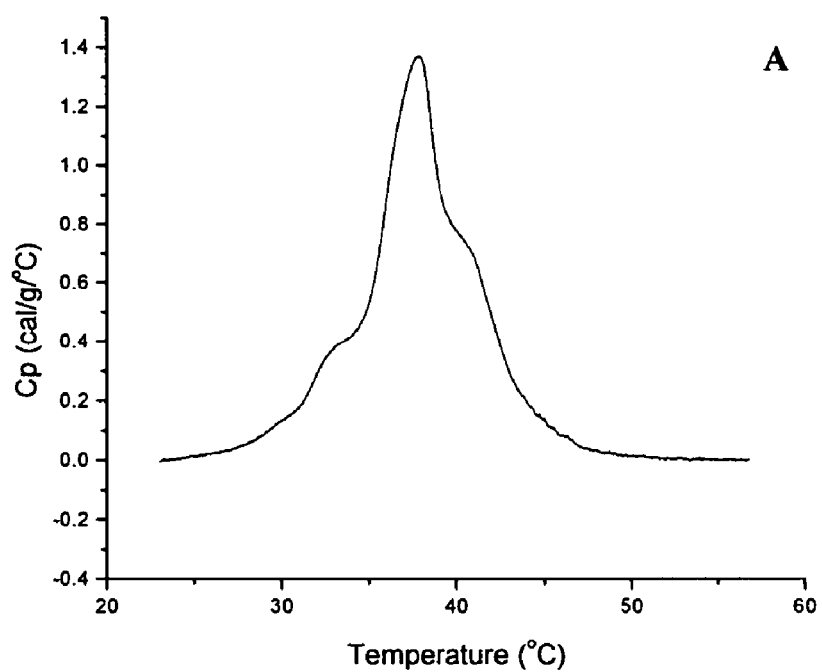
FIG. 3 depicts concentration-normalized DSC data for brain sphingomyelin (BSM) (A) or brain dihydrosphingomyelin (BDHSM) (B). Samples were scanned from 20 to 60° C. at a scan rate of 5° C./hr.
Figure 3:
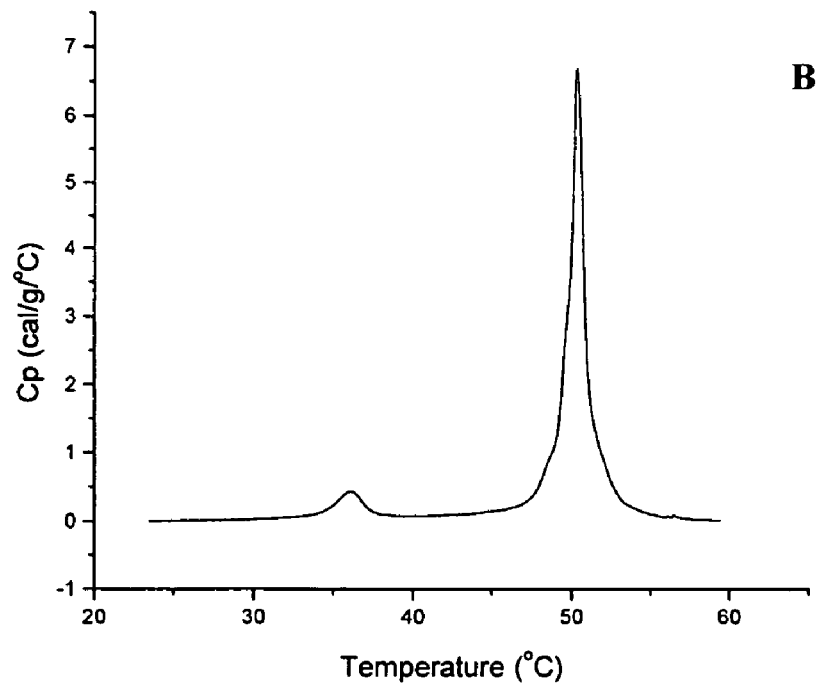

Concentration-normalized DSC scans for brain sphingomyelin (BSM) and brain dihydrosphingomyelin (BDHSM) are shown in FIG. 3. The scans show a gel to liquid-crystalline phase transition for both liposomal compositions. The phase transition for BSM is broad with a Tc of about 30° C. A narrow, single transition is seen for BDHSM with a Tc of approximately 48° C. and a distinct pre-transition is seen at about 35° C.

EXAMPLE 3

Loading of Liposomes Comprising Dihydrosphingomyelin with Topotecan at Various Temperatures The loading efficiency at different temperatures of liposomes prepared using either DHSM or SM was compared as follows.

Topotecan was loaded into liposomes comprising either DHSM or SM and cholesterol at a 55:45 (mol/mol) ratio using the A23187-ionophore method.

Lipids (ESM or EDHSM and cholesterol) were dissolved in ethanol at 65° C. at a ESM:Chol or EDHSM:Chol ratio of 55:45 mol ratio. Multilamellar vesicles (MLV) were formed by adding the hot lipid solution as a steady stream by injection with a syringe over ~30 seconds with mixing to a 353 mM $MgSO_4$/235 mM sucrose or 353 mM $MnSO_4$/235 mM sucrose solution.

The MLV were extruded at 65° C. through two stacked 80 nm polycarbonate membranes by applying nitrogen gas pressure (~200 psi) to a 10 or 100 ml Extruder. Extrusion was repeated until a vesicle size of 90 to 110 nm was achieved, which usually required 4 to 6 passes. Vesicle size was determined by quasi-elastic light scattering using a Nicomp 380 submicron particle sizer (Santa Barbara, Calif.).

The resulting large unilamellar vesicle (LUV) formulation was dialyzed against 300 mM sucrose to remove the residual ethanol and external magnesium sulphate using a tangential flow ultrafiltration system (20 wash volumes). The final preparation was concentrated to 50 mg/ml and stored at 5° C. until required for loading.

For topotecan loading, EDTA and phosphate buffer were added to liposomes (15 mg/ml total lipid, pH 6.5) at 25 mM and 50 mM final concentrations, respectively. The liposome suspensions were pre-heated to 60° C. using a water bath before the ionophore (1 μg A23187/mg lipid) was added. After a 10 min incubation, a 10 mg/ml topotecan stock solution (solubilized in 1 mg/ml tartaric acid) was added.

Figure 4:
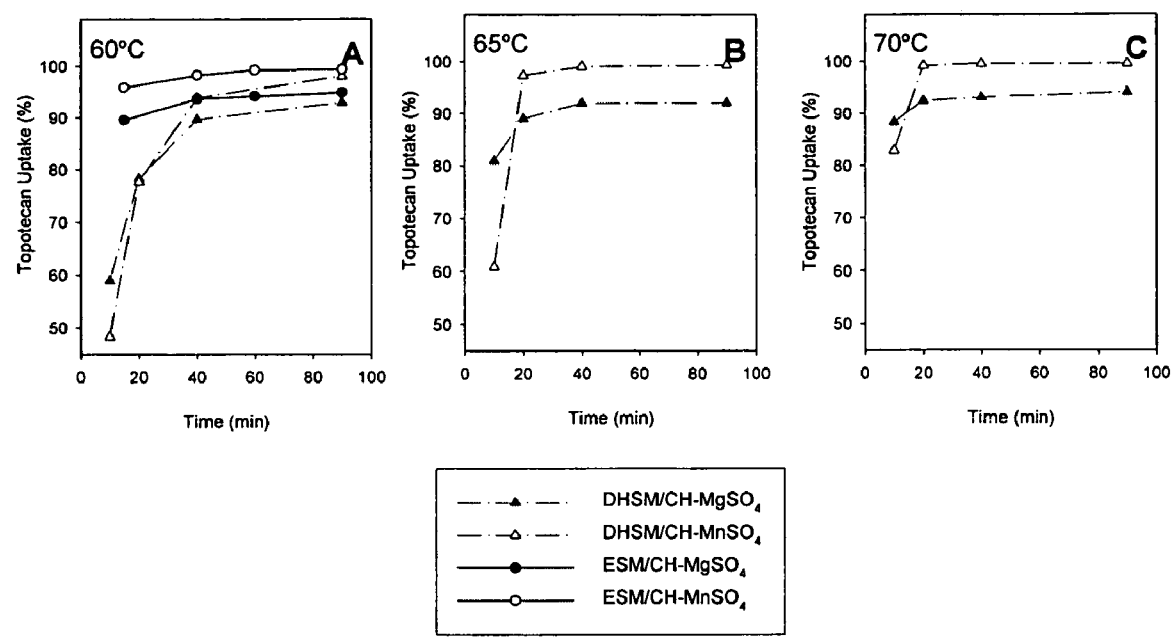
FIG. 4 graphically depicts the uptake kinetics of topotecan into various liposomal formulations. The formulations shown are ESM:Chol $Mg^{2+}$ (●); ESM $Mn^{2+}$ (○); DHSM:Chol $Mg^{2+}$ (▲); and DHSM:Chol $Mn^{2+}$ (▼).

At 60° C., ESM/CH (55:45) vesicles containing either $Mg^{2+}$ or $Mn^{2+}$ loaded rapidly with >90% uptake occurring within 15 min. (FIG. 4A). In contrast, topotecan uptake into EDHSM/CH (55:45) vesicles at 60° C. was significantly slower (FIG. 4A), requiring a minimum incubation time of ~40 min. to achieve ~90% loading of vesicles containing either $Mg^{2+}$ or $Mn^{2+}$. Higher overall encapsulation efficiencies were observed for $Mn^{2+}$-containing vesicles.

To determine if the slower uptake kinetics with EDHSM/CH (55:45) vesicles could be overcome by using a higher loading temperature, DHSM/CH (55:45) vesicles containing either $Mg^{2+}$ or $Mn^{2+}$ were loaded at 65° C. (FIG. 4B) or 70° C. (FIG. 4C). Uptake was significantly faster at both temperatures, and maximum loading was achieved after ~20 min.

These data show that encapsulation in liposomes comprising EDHSM as compared to SM is more efficient at a higher temperature, thereby demonstrating that liposomes comprising EDHSM have decreased membrane permeability than those composed of SM.

EXAMPLE 4

Characterization of In Vitro Drug Release from Liposomal Compositions Comprising Various Sphingomyelins and Dihydrosphingomyelin The in vitro drug release rates of liposomal compositions comprising vincristine encapsulated in liposomes comprising sphingomyelin derived from different sources were determined and compared. The various sources of sphingomyelin examined included egg sphingomyelin, milk sphingomyelin, and brain sphingomyelin obtained from Avanti Polar Lipids, Inc., as well as egg dihydrosphingomyelin prepared as described in Example 1. All liposomes comprised sphingomyelin and cholesterol at a 55/45 molar ratio and a drug:lipid ratio of 0.1 (w/w).

Liposomes were loaded with vincristine using standard procedures, including primarily the ionophore-mediated loading method as described in Fenske, D. B. et al., *Biochim Biophys Acta*. 1414(1-2):188-204 (1998).

Figure 5:
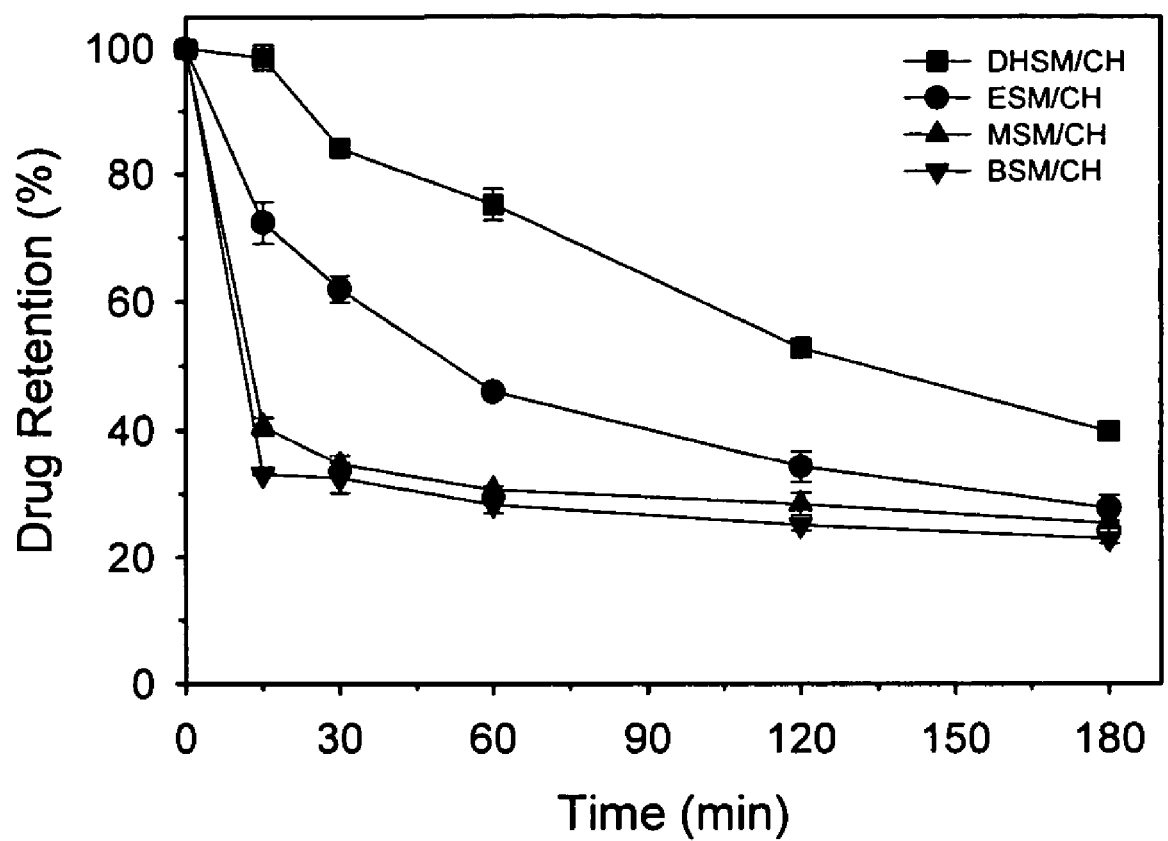
FIG. 5 depicts vincristine release from various liposome compositions on incubation in 50% FBS at 50° C. Liposome formulations include DHSM:Chol (■); ESM:Chol (●); MSM:Chol (▲); and BSM:Chol (▼).

Drug release assays were performed at 50° C. in 50% FBS, as previously described in Fenske et al. 1998, except that fetal bovine serum was used instead of mouse serum, and the temperature was increased to 50° C., from 37° C. used in Fenske et al. (1998). Drug retention was measured at various time points, and the results of these studies are depicted in FIG. 5. These results demonstrate that egg dihydrosphingomyelin dramatically increases liposome drug retention and that liposomes comprising DHSM possess remarkably superior properties for drug delivery as compared to liposomes prepared using SM.

EXAMPLE 5

Characterization of In Vitro Drug Release from Liposomal Compositions Comprising Various Dihydrosphingomyelin Species The rate of vinorelbine release from liposomes comprising various dihydrosphingomyelin species was compared in in vitro studies. Drug release rates were also determined for liposomes comprising a mixture of phospholipids, including egg dihydrosphingomyelin.

The lipids were dissolved in ethanol at 65° C. to achieve a final lipid concentration of 100 mg/ml. The hot lipid mixture was then added as a steady stream by injection with a syringe to a 353 mM $MgSO_4$/235 mM sucrose solution with mixing to form multilamellar vesicles (MLV) at final lipid and ethanol concentrations of 15 mg/ml and 15% (vol/vol), respectively. The MLV were extruded at 65° C. through two stacked 80 nm polycarbonate membranes by applying nitrogen gas pressure (~200 psi) to a 100 ml Extruder. Extrusion was repeated until a vesicle size of 90 to 110 nm was achieved, which usually required 4 to 6 passes. However, only two passes were required for EPC/CH vesicles. Vesicle size was determined by quasi-elastic light scattering using a Nicomp 380 submicron particle sizer (Santa Barbara, Calif.). The resulting large unilamellar vesicles were dialyzed against 300 mM sucrose to remove residual ethanol and external $MgSO_4$ using a tangential flow filtration system (20 wash volumes). The final preparation was concentrated to ~50 mg/ml, and an aliquot was analyzed for SM and EPC content by phosphate assay. The vesicles were stored at 5° C. until required for loading.

Vinorelbine was loaded into the SM/CH (55:45 mole ratio) liposomes using the A23187-ionophore method. EDTA and phosphate buffer were added to the liposomes (15 mg/ml total lipid, pH 6.5) at final concentrations of 25 mM and 50 mM, respectively. The liposome suspensions were pre-heated to 60° C. using a water bath before addition of the ionophore (1 μg A23187/mg lipid). After a 10 min incubation, a 10 mg/ml vinorelbine stock solution solubilized 300 mM sucrose was added at a drug to lipid ratio of 0.417 (mol/mol). This molar drug to lipid ratio is equivalent to a wt/wt ratio of 0.3 for ESM/CH vesicles. The solution was incubated for 60 min at 60° C. to induce vinorelbine encapsulation after which the ionophore, EDTA and unencapsulated topotecan were removed by tangential flow filtration using 20 wash volumes of 300 mM sucrose, 20 mM sodium phosphate, pH 6.5 buffer.

The same procedure was used for loading the EPC/CH and EPC/EDHSM/CH IVR preparations but with the following changes. An incubation temperature of 50° C. was used instead of 60° C. and the ionophore A23187 was not pre-incubated with the vesicles but added to the pre-warmed vesicles just prior to adding the vinorelbine solution. This was to minimize loss of the pH gradient due to an ionophore mediated $Na^+/H^+$ exchange. Furthermore, a 10 and 40 min incubation time was used for the EPC/CH and EPC/EDHSM/CH formulations, respectively.

Lipid (CH and ESM) and vinorelbine content was analyzed by HPLC. For vesicles containing lipids other than CH or ESM, the total lipid content was calculated based on a theoretical molar ratio of 45% for CH.

Vinorelbine release rates were compared using an in vitro release (IVR) assay. The IVR assay was conducted using a release buffer of 7 mM $NH_4Cl$, 10 mM $Na_2HPO_4$, 153 mM NaCl, pH 6.0. Briefly, the liposomal vinorelbine formulations (~0.5 ml) were diluted into 100 ml of release buffer to a final lipid content of 0.36 μmol, which is equivalent to 0.2 mg of ESM/CH (55:45 mol ratio). The mixtures were incubated in a 37° C. or 25° C. water bath and at various times aliquots were withdrawn and unencapsulated vinorelbine separated from the liposomes using Microcon YM-100 (100 kDa MW cutoff) centrifugation devices. Total and free vinorelbine content was measured by high performance liquid chromatography (HPLC).

Figure 6:
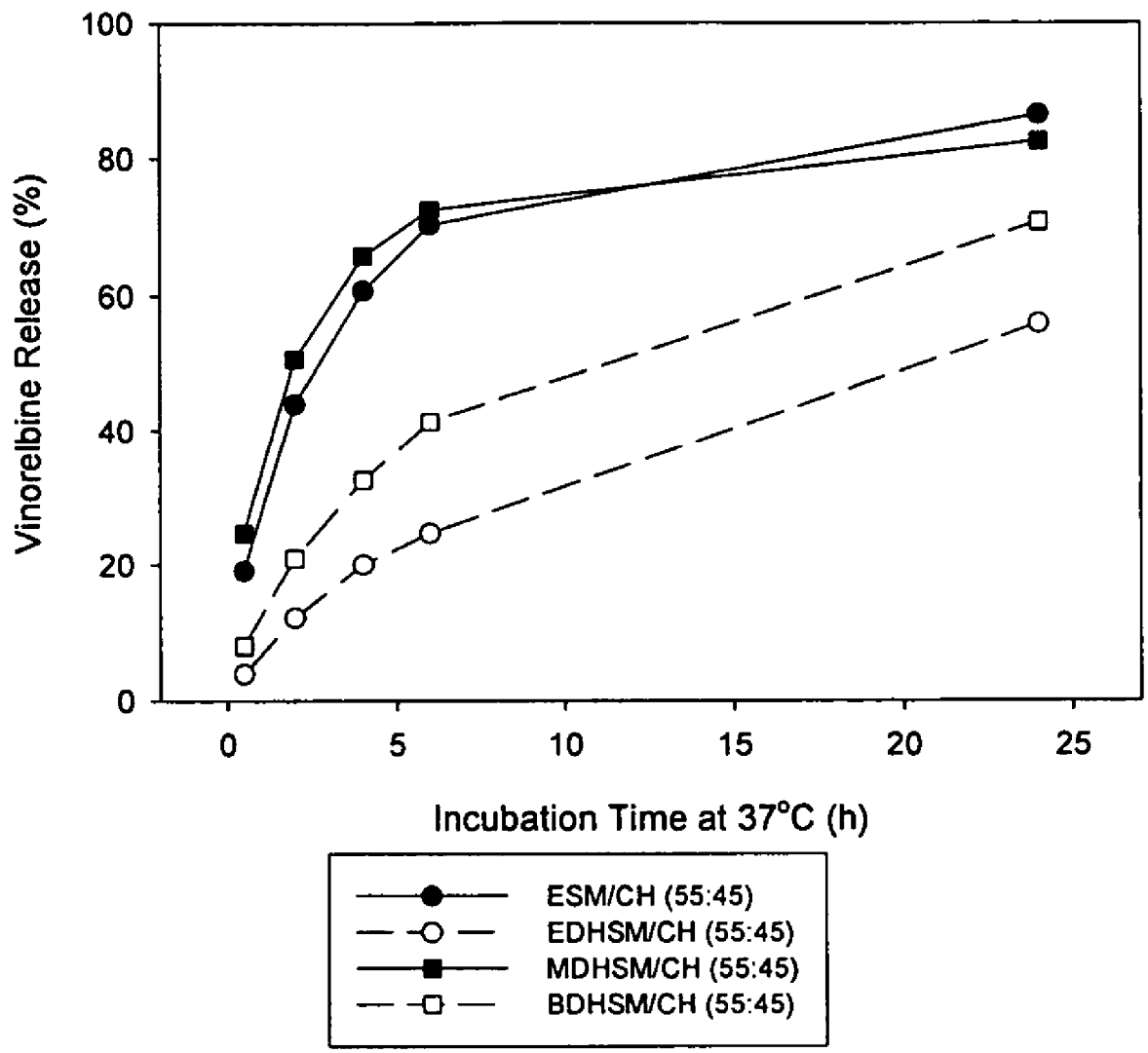
FIG. 6 depicts vinorelbine release from various liposome compositions on incubation in IVR release buffer at 37° C. The liposome compositions shown are ESM:Chol (●); MDHSM:Chol (■); BDHSM:Chol (□); and EDHSM:Chol (○).

In FIG. 6 are shown vinorelbine release rates from liposomes composed of ESM:Chol, EDHSM:Chol, BDHSM:Chol and MDHSM:Chol on incubation in the IVR release buffer at 37° C. Drug release is slowest from liposomes composed of EDHSM and BDHSM, while liposomes composed of MDHSM show a similar rate of drug release to ESM liposomes. Without wishing to be bound by any particular theory, it is noted that while EDHSM and BDHSM exhibit a narrow, single phase transition by DSC (FIG. 1 and FIG. 3), MDHSM exhibits a more complex thermotropic behavior (see FIG. 2). This may be related to the fact that the N-acyl and dihydrosphingosine chain lengths are similar in EDHSM and BDHSM (Table 1) while the majority of N-acyl chains in MDHSM are longer than the dihydrosphingosine chain by four carbon atoms or greater (Table 1). Again without wishing to be bound by any particular theory, the slower vinorelbine release rates seen for liposomes composed of EDHSM and BDHSM may result from the similar dihydrosphingosine and N-acyl chains lengths in these species.

Figure 7:
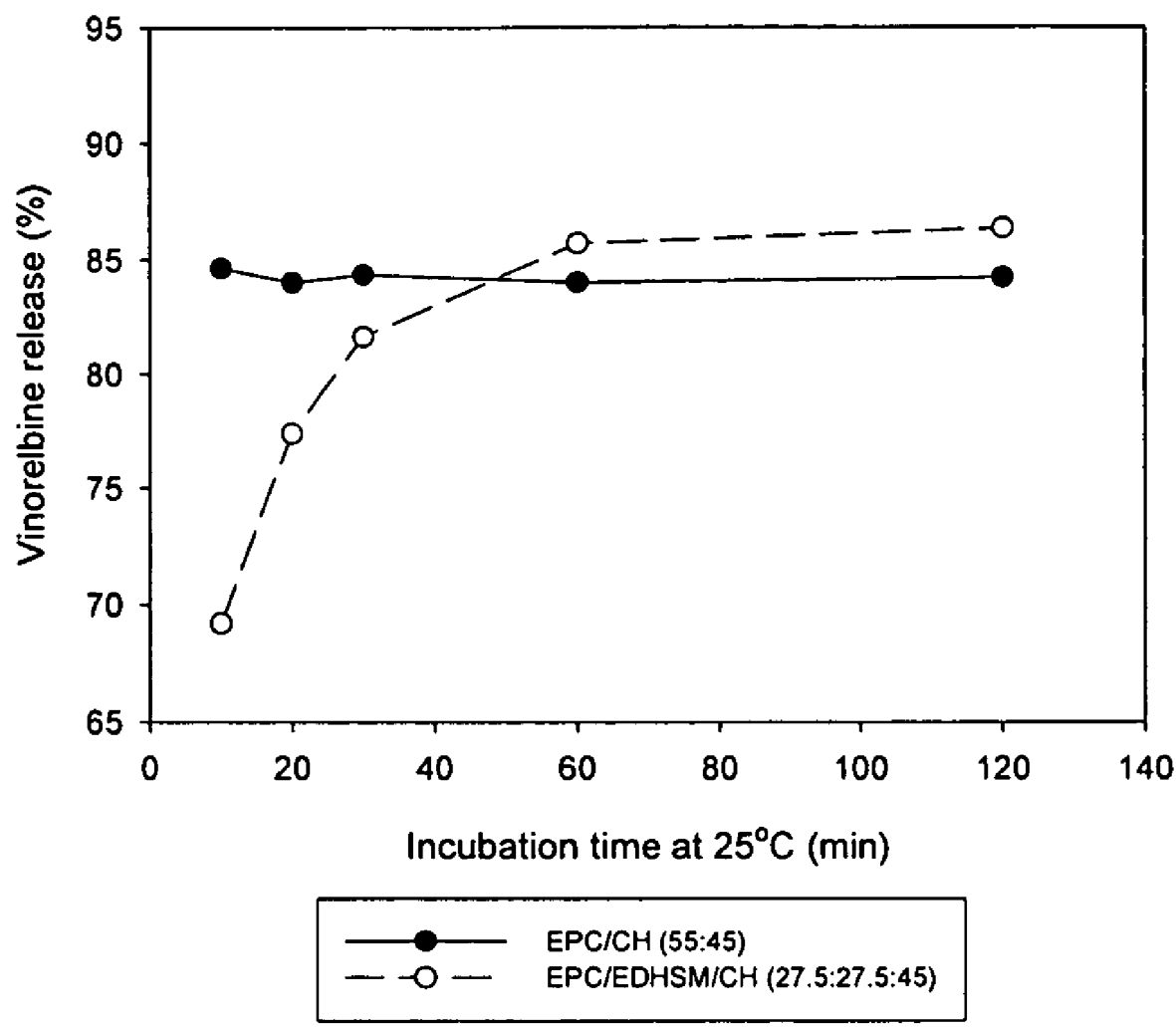
FIG. 7 depicts vinorelbine release from EPC:Chol liposomes (●) and EPC:DHSM:Chol liposomes (○) on incubation in IVR release buffer at 25° C.

In FIG. 7 are shown vinorelbine release rates from liposomes composed of EPC:Chol and EPC:EDHSM:Chol on incubation in IVR release buffer at 25° C. As can be seen, the inclusion of DHSM with EPC in liposomes results in slower vinorelbine release compared to similar vesicles containing only EPC.

EXAMPLE 6

Comparison of In Vivo Drug Release from Liposomal Compositions Comprising Egg Sphingomyelin or Egg Dihydrosphingomyelin The in vivo drug release rates of compositions comprising various drugs encapsulated in liposomes comprising either egg sphingomyelin (ESM) or egg dihydrosphingomyelin (EDHSM) were determined and compared. Liposomal compositions comprising either ESM or EDHSM were injected into ICR mice as described in Webb, M. S. et al., *Br J Cancer*

72(4):896-904 (1995) and Boman, N. L. et al., *Cancer Res.* 54(11):2830-3 (1994), and plasma drug retention was determined by standard procedures at various time points following injection. Drug retention rates for liposomal compositions comprising vincristine, NK611, or topotecan are depicted in FIGS. 8A, 8B, and 8C, respectively.

Figure 8:
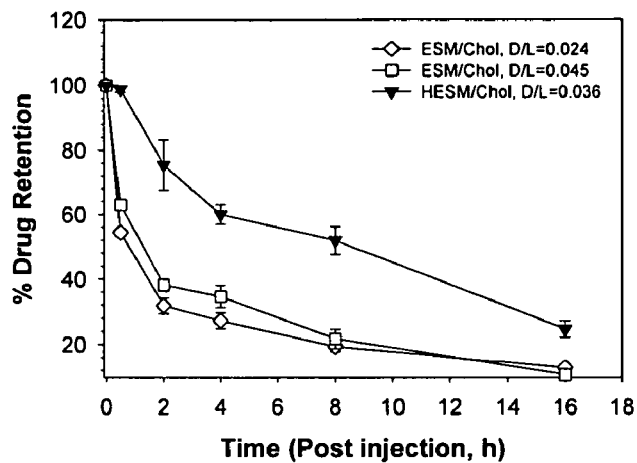
FIG. 8 depicts the in vivo plasma drug retention associated with liposomes comprising egg sphingomyelin (ESM) or egg dihydrosphingomyelin (HESM).
Figure 8:
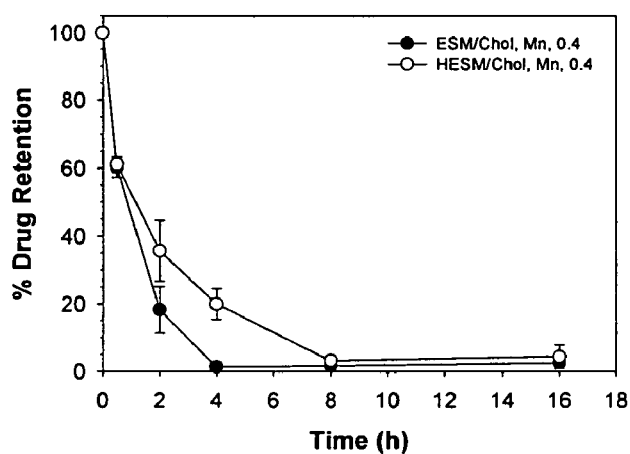
Figure 8:
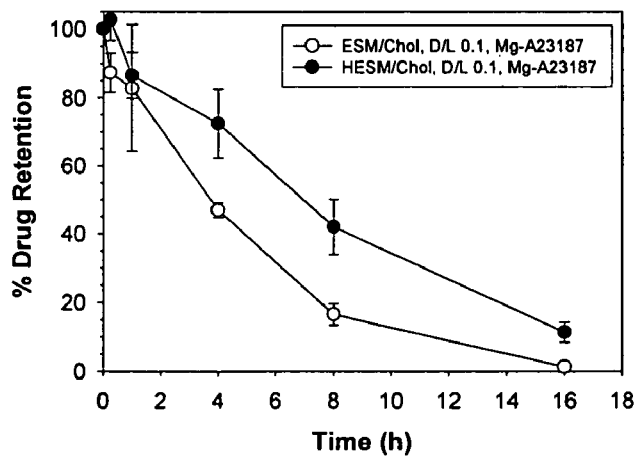

Various drug:lipid ratios and dosages were examined, as indicated in FIG. 8. Vincristine was administered at a dosage of 2 mg/kg; drug:lipid ratios are indicated on the figure. NK611 was administered at a dose of 20 mg/kg for both formulations (ESM/Chol, D/L ratio 0.36; egg-DHSM/Chol, D/L ratio 0.34). Topotecan was administered at a dose of 5 mg/kg for both formulations. In addition, for the liposomal NK611 composition the liposomes were prepared in 300 mM $Mn^{2+}$, while the liposomal topotecan compositions were prepared in magnesium at a concentration of 300 mM $Mn^{2+}$. Drug loading was by the ionophore method using A23187.

The results of these studies demonstrate that for each drug tested, compositions comprising egg dihydrosphingomyelin (egg-DHSM) exhibited markedly increased drug retention as compared to compositions comprising egg sphingomyelin (ESM) and, therefore, possess superior characteristics for in vivo drug delivery.

EXAMPLE 7

Pharmacokinetic Properties of Liposomal Topotecan Formulations Comprising Dihydrosphingomyelin Loaded Using $MG^{2+}$ or $MN^{2+}$ Pharmacokinetic (PK) studies were conducted to characterize liposomal formulation of topotecan comprising SM or DHSM. In addition, the pharmacokinetic performance of SM and DHSM formulations were compared when topotecan was loaded using the ionophore method with intravesicular $Mn^{2+}$ or $Mg^{2+}$.

Liposomal topotecan formulations were prepared and loaded essentially using an ionophore method as originally described in Fenske et al., *Biochim Biophys Acta* 1414(1-2): 188-204 (1998).

Lipids (ESM or DHSM and cholesterol) were dissolved in ethanol at 65° C. to achieve a final lipid concentration of 178 mM (equivalent to 100 mg/ml of the standard ESM/CH (55: 45 mol ratio) formulation). For formulations used in animal studies, trace amounts the radiolabeled lipid $^3$H-cholesteryl hexadecyl ether ($^3$H-CHE, 6 µmol/mol lipid; 0.55 µCi/mg lipid) were included in the lipid mixture. The $^3$H-CHE was added by first drying off the toluene solvent under a stream of nitrogen gas then re-suspending the $^3$H-CHE in the ethanol-lipid solution. Multilamellar vesicles (MLV) were formed by adding the hot lipid solution as a steady stream by injection with a syringe over ~30 seconds with mixing to a 353 mM $MgSO_4$/235 mM sucrose or 353 mM $MnSO_4$/235 mM sucrose solution.

The MLV were extruded at 65° C. through two stacked 80 nm polycarbonate membranes by applying nitrogen gas pressure (~200 psi) to a 10 or 100 ml Extruder. Extrusion was repeated until a vesicle size of 90 to 110 nm was achieved, which usually required 4 to 6 passes. Vesicle size was determined by quasi-elastic light scattering using a Nicomp 380 submicron particle sizer (Santa Barbara, Calif.).

The resulting large unilamellar vesicle (LUV) formulation was dialyzed against 300 mM sucrose to remove the residual ethanol and external magnesium sulphate using a tangential flow ultrafiltration system (20 wash volumes). The final preparation was concentrated to 50 mg/ml and stored at 5° C. until required for loading. The lipid concentration of the radiolabeled formulations for the animal study were determined from the SM content measured by using a phosphate assay. The total lipid concentration was calculated from this value by using the target mole percent of SM to CH (55:45).

Topotecan was loaded into liposomes using the A23187-ionophore method. EDTA and phosphate buffer were added to liposomes (15 mg/ml total lipid, pH 6.5) at 25 mM and 50 mM final concentrations, respectively. The liposome suspensions were pre-heated to 60° C. using a water bath before the ionophore (0.5 µg A23187/mg lipid) was added. After a 10 min incubation, a 10 mg/ml topotecan stock solution (solubilized in 1 mg/ml tartaric acid) was added. The solution was typically incubated for 60 min at 65° C. to induce topotecan encapsulation after which the ionophore, EDTA and unencapsulated topotecan were removed by tangential flow diafiltration against phosphate buffered sucrose (300 mM sucrose, 10 mM sodium phosphate, pH 6). Samples were then filtered through a 0.45 µm pore-size syringe filter followed by passage through a 0.22 µm filter before use.

All vesicles contained $^3$H-CHE to allow monitoring of the lipid clearance rates and calculation of drug-to-lipid ratios to measure drug payout in vivo.

The loading efficiency, final drug-to-lipid (D/L) ratio and vesicle size of the formulations are shown in Table 3.

TABLE 3

Summary of Liposomal Topotecan Formulations

| Lipid composition (mol ratio) | Internal cation used for loading | Vesicle size (dia., nm) | Final D/L ratio (wt/wt) | Loading efficiency (%) |
|---|---|---|---|---|
| ESM/CH (55:45) | $Mg^{2+}$ | 100 ± 24 | 0.109 | 94 |
| DHSM/CH (55:45) | $Mg^{2+}$ | 110 ± 20 | 0.109 | 92 |
| ESM/CH (55:45) | $Mn^{2+}$ | 110 ± 10 | 0.103 | 100 |
| DHSM/CH (55:45) | $Mn^{2+}$ | 100 ± 20 | 0.104 | 98 |

Mice were dosed at 50 mg lipid/kg via the lateral tail vein. Volume of injection was based on the body weight of the individual mouse (200 µl/20 g mouse). For each formulation, 4 mice were dosed per time point. Animals were anesthetized with ketamine/xylazine at 0.5, 2, 4, 8, and 16 hours, and blood was harvested by cardiac puncture. Blood was collected into EDTA vacutainer tubes and 50 µl aliquots of whole blood sample were removed for topotecan and lipid analysis. Plasma was separated by centrifugation (250×g for 10 minutes) and 50 µl aliquots were analyzed by fluorescence assay for topotecan and liquid scintillation counting for lipid, respectively.

Topotecan was recovered from blood and plasma by extracting 50 µl blood or plasma with 600 µl of cold methanol. Samples were then centrifuged at 13,400×g for 3 minutes, and 100 µl of the supernatant was removed and diluted in 700 µl methanol and 200 µl TRIS (50 mM, pH 8). Samples were measured against a standard curve (0 to 500 ng) in which blood or plasma (50 µl) was spiked with topotecan and extracted using the same protocol. Fluorescence was measured using a SLM Aminco Bowman Series 2 Luminescence Spectrometer at an excitation wavelength of 380 nm with a 2 nm band pass and an emission of 518 nm with a band pass of 4 nm.

Lipid recovery was measured with radiolabeled $^3$H-CHE. A 50 µl aliquot of blood or plasma sample from each condition was transferred to a glass scintillation vial for digestion and decolorization. For the digestion, 500 µl of Solvable was added to each vial and kept overnight at ambient temperature in the dark (>16 h). Then to decolorize, the following reagents were added: 50 µl of 200 mM EDTA (pH 7.5), 200 µl of 30% hydrogen peroxide (added cold from the fridge), and 25 µl of 10 N HCl. Sample vials were capped loosely and stored at room temperature in the dark overnight (16 h). Next, 5 ml of Pico Flour 40 was added to all vials, which were capped tightly and inverted in order to thoroughly mix the samples. All samples were loaded onto the scintillation counter (Beckman LS 6500) and measured.

Figure 9:
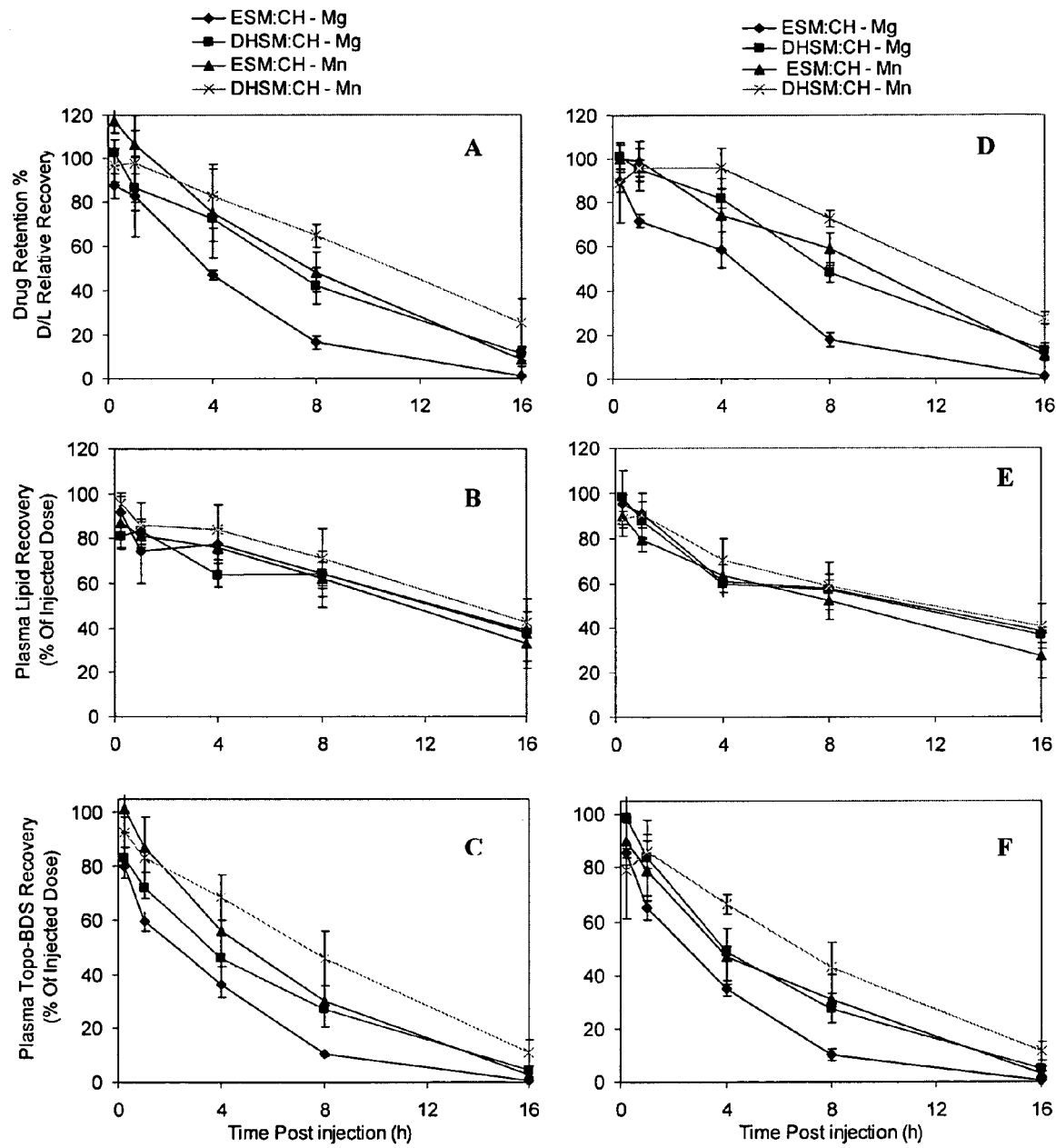
FIGS. 9A-F provides the pharmacokinetic properties of various liposomal topotecan formulations injected IV into ICR mice at 50 mg lipid/kg. Figure A-C depict recovery from plasma, while Figures D-F depict recovery from blood. Figures A and D depict drug retention over time; Figures B and E depict lipid recovery over time; and Figures C and F depict topotecan recovery over time. Data represent the average of four mice±one S.D. The liposomal compositions shown are; ESM:Chol $Mg^{2+}$ (♦); DHSM:Chol $Mg^{2+}$ (■); ESM:Chol $Mn^{2+}$ (▲); and DHSM:Chol $Mn^{2+}$ (X).

Pharmacokinetic profiles for these liposomal topotecan formulations are shown as a percentage of the starting values for the injected material at different time points (FIG. 9). Key pharmacokinetic parameters (AUC and $T_{1/2}$) were calculated from these plots and the data are presented in Table 4.

TABLE 4

Key Pharmacokinetic Parameters for Various Liposomal Topotecan Formulations

| | | AUC ± S.E.[1] | $T^{1/2}$ (h) | Upper-lower 95% conf. Limit (h) |
|---|---|---|---|---|
| BLOOD | Drug Retention | AUC (h * %) | | |
| | ESM/CH - Mg | 484 ± 16 | 2.6 | 2.0-3.8 |
| | DHSM/CH - Mg | 842 ± 16 | 5.3 | 4.0-7.7 |
| | ESM/CH - Mn | 879 ± 34 | 5.0 | 3.4-9.6 |
| | DHSM/CH - Mn | 1093 ± 19 | 9.0 | 5.4-27.1 |
| TOPOTECAN | | AUC (h * µg/mL) | | |
| | ESM/CH - Mg | 199 ± 5 | 2.1 | 1.8-2.6 |
| | DHSM/CH - Mg | 289 ± 7 | 3.6 | 3.2-4.2 |
| | ESM/CH - Mn | 299 ± 15 | 3.3 | 2.4-5.1 |
| | DHSM/CH - Mn | 375 ± 12 | 5.5 | 4.0-8.4 |
| LIPID | | AUC (h * mg/mL) | | |
| | ESM/CH - Mg | 4.9 ± 30 | 12.4 | 8.2-25.2 |
| | DHSM/CH - Mg | 4.9 ± 20 | 11.9 | 7.8-24.9 |
| | ESM/CH - Mn | 4.4 ± 0.1 | 9.6 | 8.2-11.6 |
| | DHSM/CH - Mn | 5.2 ± 0.2 | 13.7 | 11.3-17.4 |
| PLASMA | Drug Retention | AUC (h * %) | | |
| | ESM/CH - Mg | 456 ± 19 | 2.5 | 2.1-3.2 |
| | DHSM/CH - Mg | 752 ± 26 | 5.0 | 4.1-6.6 |
| | ESM/CH - Mn | 831 ± 40 | 4.3 | 3.3-6.0 |
| | DHSM/CH - Mn | 999 ± 41 | 8.1 | 5.9-12.7 |
| TOPOTECAN | | AUC (h * µg/mL) | | |
| | ESM/CH - Mg | 319 ± 9 | 2.1 | 1.7-2.8 |
| | DHSM/CH - Mg | 461 ± 17 | 3.7 | 3.0-4.9 |
| | ESM/CH - Mn | 517 ± 28 | 3.1 | 2.3-4.5 |
| | DHSM/CH - Mn | 646 ± 26 | 5.2 | 3.8-8.0 |
| LIPID | | AUC (h * mg/mL) | | |
| | ESM/CH - Mg | 9.3 ± 0.4 | 14.1 | 9.5-27.2 |
| | DHSM/CH - Mg | 9.1 ± 0.1 | 14.4 | 9.9-26.6 |
| | ESM/CH - Mn | 8.8 ± 0.3 | 11.4 | 8.5-17.3 |
| | DHSM/CH - Mn | 10.2 ± 0.3 | 14.2 | 10.4-22.5 |

[1]Standard Error

Liposomes comprising egg SM (ESM) and cholesterol and loaded with topotecan using a $Mg^{2+}$ ion gradient exhibited the fastest topotecan release rate (FIGS. 9A, 9D and Table 4; $T_{1/2}$~2.6 h). Similar liposomes loaded with topotecan using $Mg^{2+}$ but composed of egg dihydrosphingomyelin (DHSM), show slower drug release (FIGS. 9A, 9D and Table 4) and exhibit a corresponding increase in AUC for drug retention and a longer drug release half-life (Table 4). Similarly when liposomes composed of ESM and DHSM but loaded with topotecan using $Mn^{2+}$ are compared, drug release is also slower for the DHSM formulation (FIGS. 9A and 9B). Again the DHSM liposomes exhibit a higher AUC for drug retention and a longer drug release half-life (Table 4).

At the lipid doses used in this study, the rate of liposome clearance from the blood/plasma compartment was not significantly different for liposomes composed of ESM or DHSM (FIGS. 9B and 9E and Table 4) over 16 hours. However, as shown in Example 9, at lower lipid doses, liposomes composed of DHSM are cleared from the blood compartment more slowly than similar liposomes composed of ESM.

The reduced rate of topotecan release from liposomes composed of DHSM is also reflected in the topotecan pharmacokinetics. Blood and plasma drug levels are higher for the two DHSM formulations ($Mn^{2+}$ and $Mg^{2+}$) compared to their corresponding ESM counterparts (FIGS. 9C and 9F). This results in higher drug AUCs and longer drug circulation half-lives for the DHSM formulations compared to the ESM formulations (Table 4).

In summary, these data indicate that liposomal drug formulations comprising DHSM possess surprisingly superior pharmacokinetic properties in comparison to previously described liposomal drug formulations.

EXAMPLE 8

Pharmacokinetic Properties of Liposomal Vinorelbine Formulations Comprising Dihydrosphingomyelin Loaded Using $MG^{2+}$ or $MN^{2+}$ Pharmacokinetic (PK) studies were conducted to characterize liposomal formulations of vinorelbine comprising SM or DHSM. In addition, the pharmacokinetic performance of SM and DHSM formulations were compared when vinorelbine was loaded using the ionophore method with intravesicular $Mn^{2+}$ or $Mg^{2+}$.

Liposomes of ESM or DHSM were prepared as described in Example 5 containing either $Mn^{2+}$ or $Mg^{2+}$ as the intravesicular cation. Vinorelbine was loaded into the liposomes using the ionophore method with A23187, as described in Example 5, at drug/lipid ratios of either 0.1 or 0.3 (target ratios).

The pharmacokinetic properties of the liposomal vinorelbine formulations were determined in ICR mice as described for liposomal topotecan in Example 7. Liposome and vinorelbine concentrations in blood and plasma were determined by liquid-scintillation counting for $^3$H-CHE (liposome concentration) and by HPLC analysis (vinorelbine concentration).

Pharmacokinetic profiles for these liposomal vinorelbine formulations were determined and key pharmacokinetic parameters (AUC and $T_{1/2}$) were calculated from these plots (Table 5).

TABLE 5

Key Pharmacokinetic Parameters (Plasma) for Various Liposomal Vinorelbine Formulations

| Initial Drug:Lipid Ratio | | AUC ± S.E.[1] | T½ (h) | Upper-lower 95% conf. Limit (h) |
|---|---|---|---|---|
| Drug:Lipid Ratio 0.31 | Drug Retention | AUC (h * %) | | |
| | ESM/CH - Mg | 1130 ± 24 | 8.6 | 6.8-11.9 |
| | DHSM/CH - Mg | 1564 ± 22 | 12.7 | 8.6-24.6 |
| | ESM/CH - Mn | 1429 ± 37 | 8.0 | 5.1-19.2 |
| | DHSM/CH - Mn | 1948 ± 21 | 19.5 | 11.8-55.4 |
| | VINORELBINE | AUC (h %) | | |
| | ESM/CH - Mg | 584 ± 27 | 4.1 | 3.1-5.8 |
| | DHSM/CH - Mg | 713 ± 26 | 5.3 | 4.6-6.2 |
| | ESM/CH - Mn | 687 ± 22 | 4.3 | 3.2-6.7 |
| | DHSM/CH - Mn | 860 ± 27 | 5.8 | 4.4-8.7 |
| | LIPID | AUC (h * %) | | |
| | ESM/CH - Mg | 707 ± 30 | 7.6 | 5.6-12.0 |
| | DHSM/CH - Mg | 656 ± 25 | 8.9 | 7.1-12.1 |
| | ESM/CH - Mn | 692 ± 30 | 11.0 | 8.8-14.6 |
| | DHSM/CH - Mn | 650 ± 20 | 8.2 | 6.0-12.9 |
| Drug:Lipid Ratio 0.1 | Drug Retention | AUC (h * %) | | |
| | ESM/CH - Mg | 876 ± 18 | 6.6 | 5.0-9.6 |
| | DHSM/CH - Mg | 1067 ± 11 | 11.0 | 7.2-23.2 |
| | ESM/CH - Mn | 1266 ± 11 | 14.9 | 9.6-32.4 |
| | DHSM/CH - Mn | 1522 ± 46 | 31.3 | 17.2-177.0 |
| | VINORELBINE | AUC (h * µg/mL) | | |
| | ESM/CH - Mg | 1842 ± 50 | 3.9 | 2.9-6.0 |
| | DHSM/CH - Mg | 1856 ± 31 | 6.2 | 5.2-7.8 |
| | ESM/CH - Mn | 2477 ± 80 | 6.5 | 5.3-8.6 |
| | DHSM/CH - Mn | 2481 ± 71 | 8.3 | 5.8-14.6 |
| | LIPID | AUC (h * mg/mL) | | |
| | ESM/CH - Mg | 9.02 ± 0.22 | 10.1 | 7.4-15.7 |
| | DHSM/CH - Mg | 7.92 ± 0.18 | 14.4 | 11.7-18.6 |
| | ESM/CH - Mn | 8.50 ± 0.32 | 11.3 | 9.5-13.9 |
| | DHSM/CH - Mn | 7.68 ± 0.18 | 10.9 | 8.2-16.2 |

[1]Standard Error

Liposomal formulations of vinorelbine comprising DHSM showed slower drug release in vivo, as indicated by higher drug retention AUC values and longer drug release half-lives, compared to similar liposomes comprised of ESM (Table 5). This improved vinorelbine retention by DHSM liposomes compared to ESM liposomes was seen for formulations loaded at a 0.1 drug:lipid ratio and formulations loaded at a 0.31 drug:lipid ratio. Similarly, DHSM liposomes loaded with vinorelbine using either $Mn^{2+}$ or $Mg^{2+}$, showed slower vinorelbine release in vivo compared to similar ESM liposomes loaded using either $Mn^{2+}$ or $Mg^{2+}$ (Table 5).

In summary, these results surprisingly demonstrate that DHSM liposomes provide slower release of encapsulated vinorelbine compared to ESM liposomes over a wide range of drug:lipid ratios and using different loading procedures.

EXAMPLE 9

Plasma Circulation Half-Life of Dihydrosphingomyelin Liposomes

Liposomes comprising ESM:cholesterol or DHSM:cholesterol were prepared using similar procedures to those described in Examples 7 and 8, and incorporating the radiolabeled lipid marker $^3$H-CHE. The plasma residency of these liposomes after intravenous injection into mice was then compared at two lipid doses (25 mg/m$^2$ and 250 mg/m$^2$).

Figure 10:
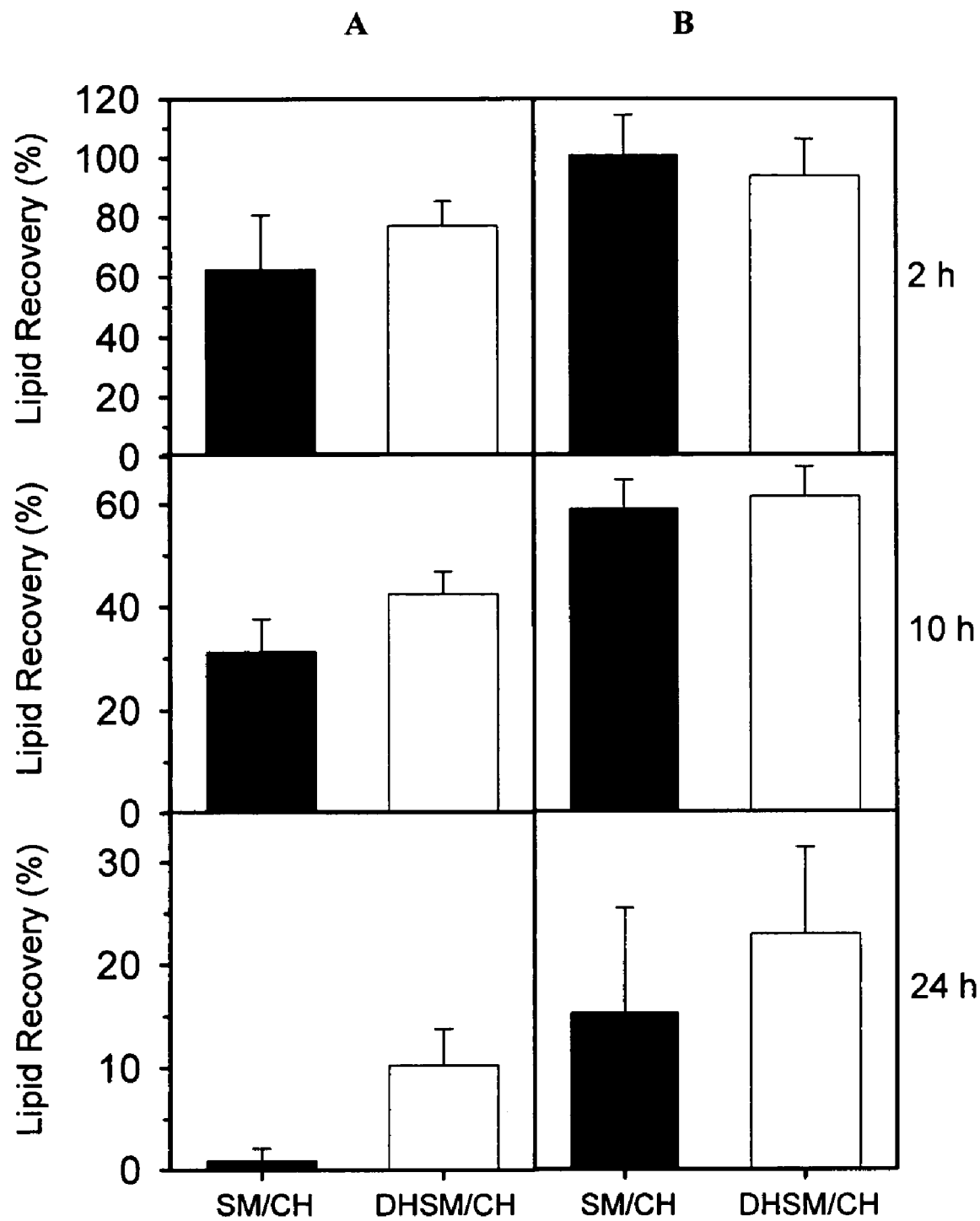
FIG. 10 depicts plasma levels of ESM:Chol or DHSM:Chol liposomes at various times after intravenous injection for two lipid dose levels: (A) 25 mg/m² and (B) 250 mg/m².

As shown in FIG. 10, DHSM liposomes remain in the plasma compartment longer than similar liposomes containing ESM, particularly at lower lipid doses and at longer timepoints. For drug delivery applications, circulation lifetime is important because the longer the liposomes remain in the plasma compartment, the greater the likelihood that they will accumulate at a disease site, for example within a tumor. A longer circulation lifetime can, therefore, result in greater drug delivery to the disease site.

These results demonstrate that in addition to providing slower drug release in vivo, DHSM liposomes also exhibit a longer circulation half-life compared to similar liposomes composed of ESM. This unexpected property can further enhance the pharmacokinetic behaviour of drugs encapsulated in liposomes of the present invention.

EXAMPLE 10

Antitumor Activity of Liposomal Topotecan Formulations Comprising Dihydrosphingomyelin The antitumor activity of liposomal formulations of topotecan comprising ESM or DHSM were evaluated in human tumor xenograft models having significant (MX-1 (breast)) and modest (HT-29 (colon)) sensitivity to free topotecan at its maximum therapeutic dose (MTD). These studies also evaluated the influence of intravesicular cation composition ($Mn^{2+}$ or $Mg^{2+}$) on antitumor activity.

Liposomal formulations comprising ESM or DHSM and containing topotecan were prepared as described in Example 7. Topotecan loading was conducted with either $Mg^{2+}$ or $Mn^{2+}$ as the intravesicular cation.

DHSM/Chol (55/45, mol/mol) and ESM/Chol (55/45, mol/mol) liposome formulations were prepared and loaded using an ionophore method as originally described in Fenske et al., *Biochim Biophys Acta* 1414(1-2): 188-204 (1998) and described in more specific detail in Example 4. Liposomes (15 mg/mL) containing 200 mM sucrose and ~300 mM $MnSO_4$ or $MgSO_4$ were incubated with A23187 ionophore (0.5 μg/mg of lipid) in 300 mM sucrose, 25 mM EDTA, and 50 mM phosphate buffer (pH 6.0). This mixture was warmed for 10 min at 65° C. Topotecan (10 mg/ml in 1 mg/mL tartaric acid, 300 mM sucrose) was added to achieve a drug-to-lipid ratio of 0.1 (wt/wt) and drug loading occurred during a 60 min incubation at 65° C. To remove non-encapsulated topotecan, ionophore and EDTA, the incubation mixture was dialyzed at room temperature against 20 volumes of phosphate-buffered sucrose (10 mM sodium phosphate, 300 mM sucrose; pH 6.0) using a Midgee™ HOOP™ ultrafiltration cartridge (M.Wt. cutoff 100,000; Amersham Biosciences). Samples were filtered through a 0.22 μm filter prior to vialing.

Liposomal topotecan formulations were diluted to the appropriate drug concentration using sterile 10 mM sodium phosphate, 300 mM sucrose, pH 7.4, in preparation for animal injections. All formulations were injected intravenously via the lateral tail vein of female, 6-8 week old, athymic Crl:CD-1®-nuBR mice obtained from Charles River Laboratories (Quebec, Canada). Experimental groups consisted of 8 or 5 mice for MX-1 and HT-29 studies, respectively. The dosing volume of each formulation was 10 mL/kg body weight. For the study with MX-1 xenografts, sample injections were q7d×3, beginning on day 13 post-tumor implantation. For the HT-29 xenograft study, sample injections were q4d×3, beginning on day 9 post-tumor implantation.

MX-1 human mammary carcinoma tumor fragments were obtained from the Division of Cancer Treatment and Diagnosis (DCTD) Tumor Repository (Frederick, Md.), maintained by serial passage in vivo, and implanted by trocar into the dorsal flank of the nude mice. HT-29 human colon adenocarcinoma cells were obtained from the American Type Culture Collection (ATCC; Manassas, Va.) and maintained in vitro in McCoy's 5A medium supplemented with 10% fetal bovine serum and 2 mM L-glutamine. On day 0, tumor cells ($5 \times 10^6$) were implanted via subcutaneous (s.c.) injection into the dorsal flank. Treatments were initiated when tumor volumes were 100-300 $mm^3$. Tumors were measured at least three times per week with calipers and tumor volume ($mm^3$) was calculated using the formula: (length×$width^2$)/2, where width was the smaller of the two perpendicular measurements (Fiebig H-H and Burger A M, In: *Tumor Models in Cancer Research* (Ed. Teicher B A), pp. 113-137. Humana Press Inc, Totowa (2002).

Therapeutic activity was evaluated by several criteria, as discussed in detail in Plowman et al. In: *Anticancer Drug Development Guide: Preclinical Screening, Clinical Trials, and Approval* (Ed. Teicher B). Humana Press Inc., Totowa (1997). Calculated tumor parameters included: (i) tumor growth delay (T-C); the mean difference in time (days) for treated and control tumors to reach 1000 $mm^3$; (ii) partial regressions (PR) and complete regressions (CR); a PR was scored when a tumor decreased to ≦50% of its initial size but remained above the limit of measurability (63 $mm^3$); a CR was scored when a tumor regressed below 63 $mm^3$ but ultimately showed regrowth; and (iii) tumor free animals (TF) were scored when a tumor regressed below 63 $mm^3$ and remained below this level up to and including the final observation day.

Figure 11:
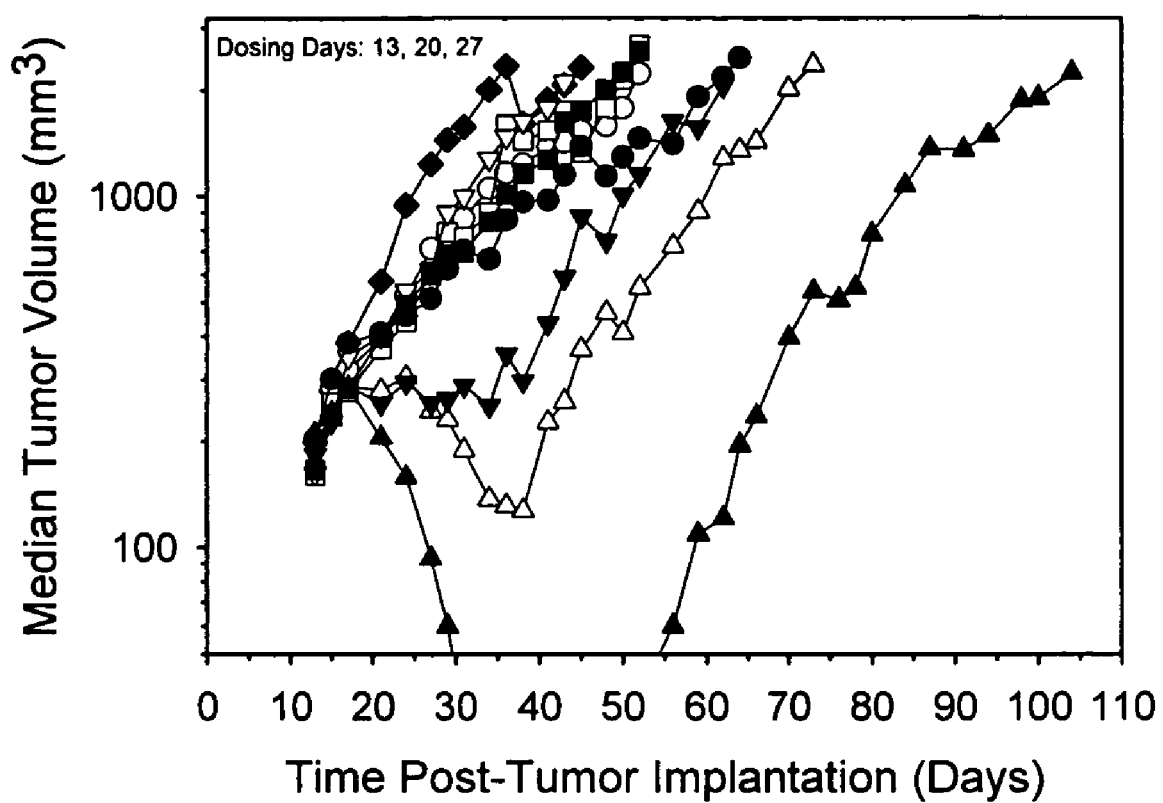
FIG. 11 provides a graphical representation of the antitumor activity of ESM/Chol and DHSM/Chol liposomal topotecan formulations in MX-1 xenografts. All doses indicated were administered i.v. q7d×3. The symbols represent: saline control (♦); ESM/Chol/$Mg^{2+}$, 1.0 mg/kg (○); ESM/Chol/$Mg^{2+}$, 0.5 mg/kg (□); DHSM/Chol/$Mg^{2+}$, 1.0 mg/kg (Δ); DHSM/Chol/$Mg^{2+}$, 0.5 mg/kg (∇); ESM/Chol/$Mn^{2+}$ 1.0 mg/kg (●); ESM/Chol/$Mn^{2+}$, 0.5 mg/kg (■); DHSM/Chol/$Mn^{2+}$, 1.0 mg/kg (A); and DHSM/Chol/$Mn^{2+}$, 0.5 mg/kg (V). Data points represent median tumor volumes (n=8). For graphical purposes, measured tumor volumes below 63 mm³, the NCI defined limit of measurability, were cut-off at 40 mm³.

In FIG. 11 are shown tumor growth rates in the MX-1 model for untreated control animals and for animals treated with the liposomal topotecan formulations. Antitumor activity parameters are summarized in Table 6.

TABLE 6

Summary of antitumor activity parameters - MX-1 mammary xenografts

| Topotecan Formulation | Topotecan Dose (mg/kg) | Internal Cation | T-C (days) | PR/CR/TF n = 8 |
|---|---|---|---|---|
| ESM/Chol | 1.0 | $Mg^{2+}$ | 7.6 | 0/0/0 |
| ESM/Chol | 0.5 | $Mg^{2+}$ | 8.2 | 0/0/0 |
| DHSM/Chol | 1.0 | $Mg^{2+}$ | 33.8 | 1/2/1 |
| DHSM/Chol | 0.5 | $Mg^{2+}$ | 5.8 | 0/0/0 |
| ESM/Chol | 1.0 | $Mn^{2+}$ | 14.3 | 0/1/0 |
| ESM/Chol | 0.5 | $Mn^{2+}$ | 10.4 | 0/0/0 |
| DHSM/Chol | 1.0 | $Mn^{2+}$ | 57.7 | 0/4/4 |
| DHSM/Chol | 0.5 | $Mn^{2+}$ | 24.9 | 1/2/0 |

Figure 12:
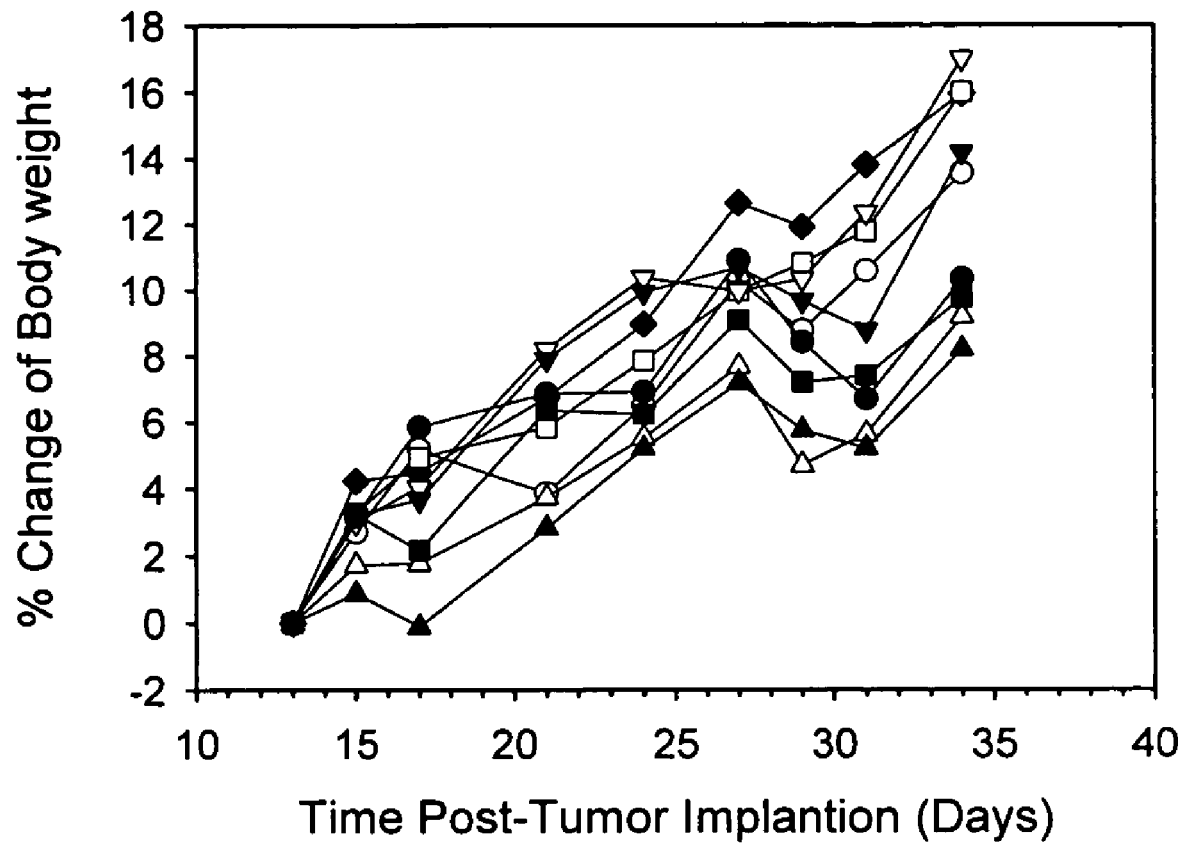
FIG. 12 depicts treatment-related changes in body weights in the MX-1 study. The percentage change in body weight was monitored during the dosing phase (i.v. q7d×3) of the MX-1 study. The symbols represent: saline control (♦); ESM/Chol/$Mg^{2+}$, 1.0 mg/kg (○); ESM/Chol/$Mg^{2+}$, 0.5 mg/kg (□); DHSM/Chol/$Mg^{2+}$, 1.0 mg/kg (Δ); DHSM/Chol/$Mg^{2+}$, 0.5 mg/kg (∇); ESM/Chol/$Mn^{2+}$ 1.0 mg/kg (●); ESM/Chol/$Mn^{2+}$, 0.5 mg/kg (■); DHSM/Chol/$Mn^{2+}$, 1.0 mg/kg (▲); and DHSM/Chol/$Mn^{2+}$, 0.5 mg/kg (▼). Data points represent group means for percentage change in body weight (n=8).

Antitumor activities are consistent with the pharmacokinetic properties of these formulations. When topotecan is loaded using $Mg^{2+}$ a significantly longer delay in tumor growth (T-C) is seen for the DHSM formulation at both 1.0 and 0.5 mg/kg compared to the ESM formulation at these same doses (Table 6). Further, only in the DHSM formulation (1 mg/kg) is a tumor-free animal seen, as well as complete and partial tumor responses. Similarly, for formulations loaded using $Mn^{2+}$ as the intravesicular cation, tumor growth delays were considerably longer for the DHSM formulation compared to the ESM formulation. Further, only for the DHSM formulation (1 mg/kg) were all treated animals either complete responders (CR) or tumor free survivors (TF) (Table 6). This study also evaluated the toxicities of these liposomal topotecan formulations based on animal weight loss. As shown in FIG. 12, no significant weight loss was seen in any treatment group. This indicates that, in addition to showing good antitumor activity, the DHSM formulations were well tolerated.

Figure 13:
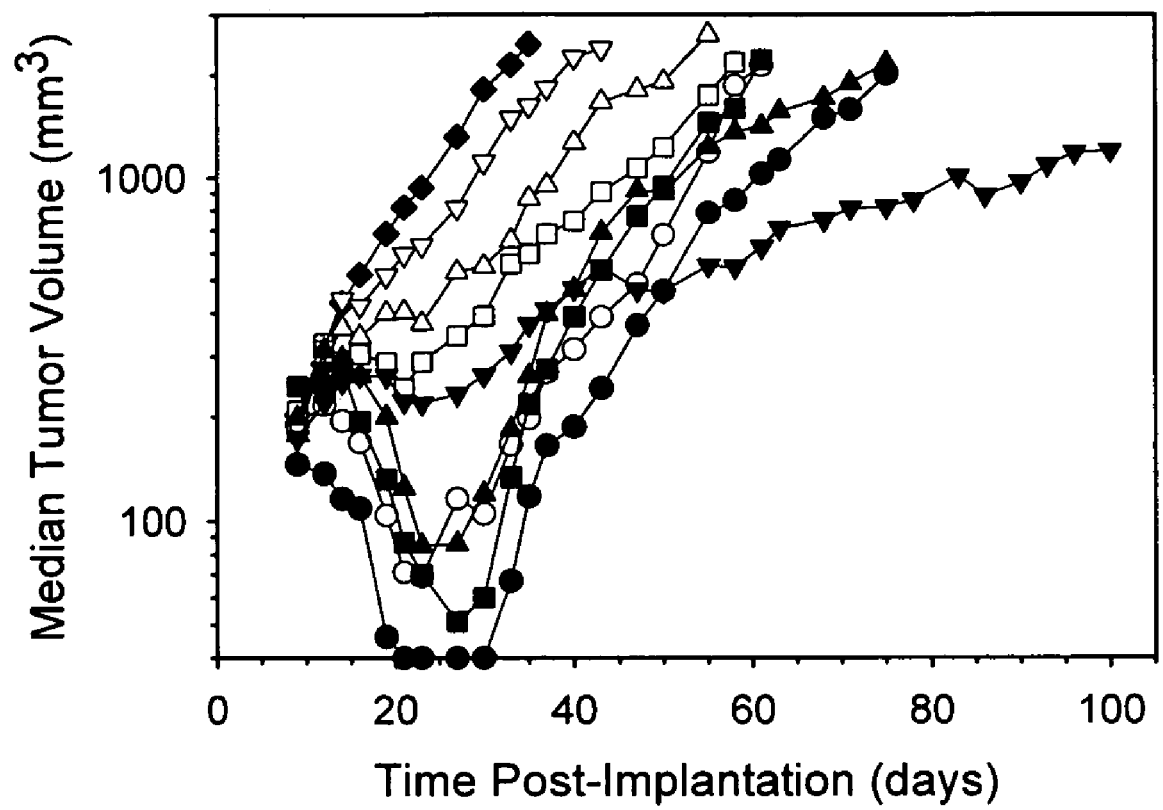
FIG. 13 provides a graphical representation of the antitumor activity of ESM/Chol/$Mg^{2+}$ and DHSM/Chol/$Mn^{2+}$ liposomal topotecan formulations in HT-29 xenografts. All doses listed were administered i.v. q4d×3. The symbols represent: saline control (♦); ESM/Chol/$Mg^{2+}$, 4.0 mg/kg (○); ESM/Chol/$Mg^{2+}$, 2.0 mg/kg (□); ESM/Chol/$Mg^{2+}$, 1.0 mg/kg (Δ); ESM/Chol/$Mg^{2+}$, 0.5 mg/kg (∇); DHSM/Chol/$Mn^{2+}$, 4 mg/kg (●); DHSM/Chol/$Mn^{2+}$, 2.0 mg/kg (■); DHSM/Chol/$Mn^{2+}$, 1.0 mg/kg (▲); and DHSM/Chol/$Mn^{2+}$, 0.5 mg/kg (▼). Data points represent median tumor volumes (n=5). For graphical purposes, measured tumor volumes below 63 mm³, the NCI defined limit of measurability, were cut-off at 40 mm³.

Antitumor activity was also evaluated in the HT-29 colon xenograft model. In this study, animals were treated either with liposomes comprising ESM loaded with topotecan using $Mg^{2+}$ or liposomes comprising DHSM loaded with topotecan using $Mn^{2+}$. Animals treated with the ESM/Chol/$Mg^{2+}$ formulation of liposomal topotecan in this model showed marginal or modest activity after i.v. injection using a q4d×3 dosing schedule (FIG. 13). At the highest dose (4.0 mg/kg/dose), T-C was 29.3 days and two partial and three complete responses were observed out of five mice (Table 7). The DHSM/Chol/$Mn^{2+}$ formulation showed improved antitumor activity in this model, with a T-C of 37.2 days at 4.0 mg/kg (q4d×3, i.v.) and four complete responses and one tumor free animal out of five mice. Partial and complete responses were also observed in the next two dosing groups (1.0 and 2.0 mg/kg/dose).

TABLE 7

Summary of antitumor activity parameters - HT-29 colon xenograft model

| Topotecan Formulation | Topotecan Dose (mg/kg) | Internal Cation | T-C (days) | PR/CR/TF n = 5 |
|---|---|---|---|---|
| ESM/Chol | 4.0 | $Mg^{2+}$ | 29.3 | 2/3/0 |
| ESM/Chol | 2.0 | $Mg^{2+}$ | 21.3 | 0/0/0 |
| ESM/Chol | 1.0 | $Mg^{2+}$ | 13.4 | 0/0/0 |
| ESM/Chol | 0.5 | $Mg^{2+}$ | 4.8 | 0/0/0 |
| DHSM/Chol | 4.0 | $Mn^{2+}$ | 37.2 | 0/4/1 |
| DHSM/Chol | 2.0 | $Mn^{2+}$ | 27.3 | 2/3/0 |
| DHSM/Chol | 1.0 | $Mn^{2+}$ | 22.6 | 0/2/0 |
| DHSM/Chol | 0.5 | $Mn^{2+}$ | 63.1 | 0/0/0 |

Figure 14:
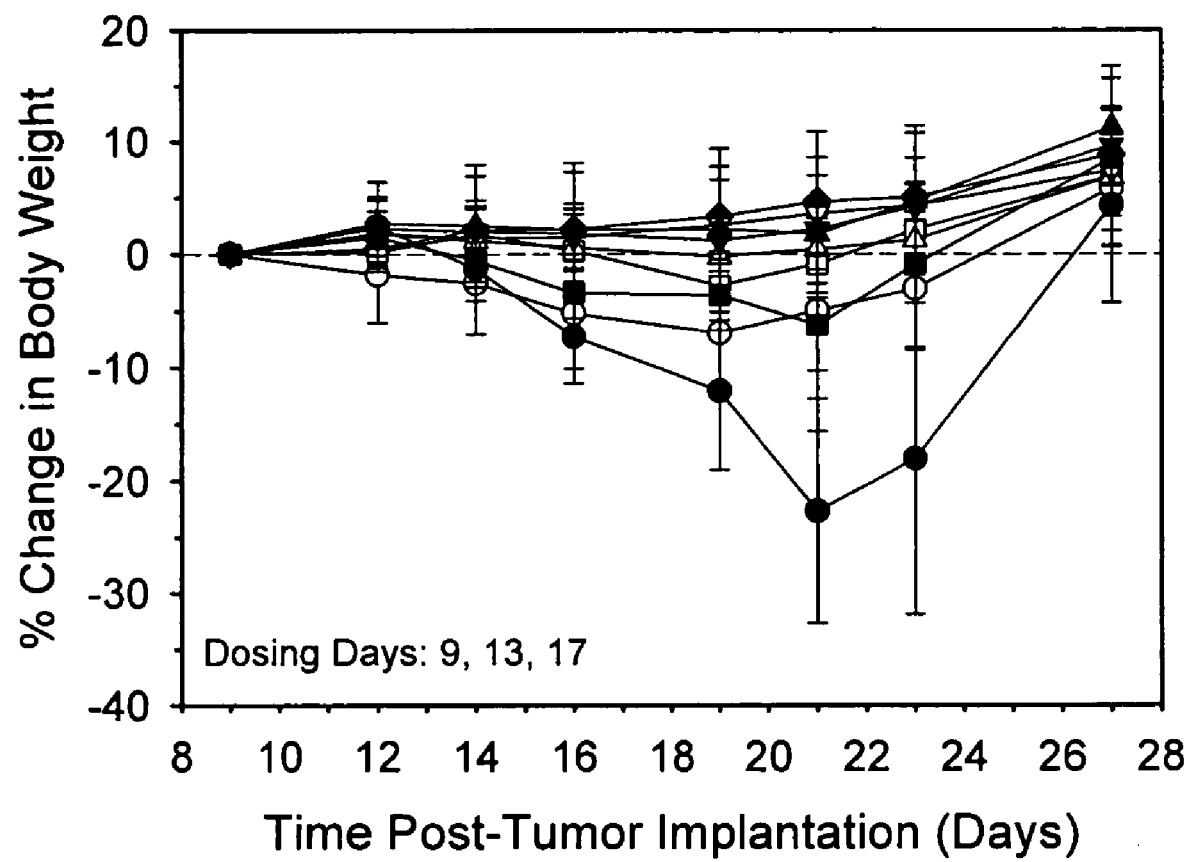
FIG. 14 depicts treatment-related changes in body weights in the HT-29 study. The percentage change in body weight was monitored during the dosing phase (i.v. q4d×3) of the HT-29 study. The symbols represent: saline control (♦); ESM/Chol/Mg2+, 4.0 mg/kg (○); ESM/Chol/Mg2+, 2.0 mg/kg (□); ESM/Chol/Mg2+, 1.0 mg/kg (Δ); ESM/Chol/Mg2+, 0.5 mg/kg (∇); DHSM/Chol/Mn2+4 mg/kg (●); DHSM/Chol/Mn2+, 2.0 mg/kg (■); DHSM/Chol/Mn2+, 1.0 mg/kg (▲); and DHSM/Chol/Mn2+, 0.5 mg/kg (▼). Data points represent group means for percentage change in body weight (±standard deviation; n=5).

Treatment-related changes in total body weight were monitored during the dosing phase. Static or increasing mean group weights were observed at the two lowest treatment doses for both liposomal topotecan formulations examined. In the HT-29 model, which was dosed more aggressively at q4d×3, a significant and progressive decrease in weight (~23%) was observed during the dosing phase with the high dose (4.0 mg/kg/dose) DHSM/Chol/$Mn^{2+}$ formulation (FIG. 14). In contrast, the same dose and schedule for the ESM/Chol/$Mg^{2+}$ formulation resulted in a maximum group weight loss of ~6%. The increased weight loss for the DHSM/Chol/$Mn^{2+}$ formulation is consistent with increased drug retention for this formulation and maintenance of the drug in the active lactone form, compared with the ESM/Chol/$Mg^{2+}$ formulation. All other dosing levels and formulations examined in this study exhibited maximum weight losses <5% or showed progressive weight gain.

In summary, the improved antitumor activity of liposomal topotecan comprising DHSM in both MX-1 and HT-29 xenografts demonstrates that a higher plasma topotecan AUC results in an improved efficacy profile against human xenograft models and supports the clinical efficacy of liposomal topotecan formulations comprising DHSM.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A liposomal composition comprising a liposome, wherein said liposome comprises phospholipid and cholesterol at a molar ratio from 75/25 (mol/mol) total phospholipid/cholesterol to 25/75 (mol/mol) total phospholipid/cholesterol, wherein at least 20% (molar basis) of total phospholipid present in said liposome is dihydrosphingomyelin (DHSM), wherein the interior of said liposome comprises $MnSO_4$ or $MgSO_4$, and wherein said liposome comprises a therapeutic agent.

2. The liposomal composition of claim 1, wherein said DHSM constitutes at least 50% (molar basis) of total phospholipid present in said liposome.

3. The liposomal composition of claim 1, wherein the N-acyl chain of said DHSM consists of 12 to 24 carbon atoms.

4. The liposomal composition of claim 1, wherein the DHSM is selected from the group consisting of: N-palmitylsphinganyl-1-O-phosphorylcholine; N-stearylsphinganyl-1-O-phosphorylcholine; N-myristylsphinganyl-1-O-phosphorylcholine; and N-arachidylsphinganyl-1-O-phosphorylcholine.

5. The liposomal composition of claim 1, wherein the DHSM N-acyl and dihydrosphingosine chains comprise carbon chains that are not different in length by more than four carbon atoms.

6. The liposomal composition of claim 1, wherein the therapeutic agent is an antineoplastic agent.

7. The liposomal composition of claim 6, wherein the antineoplastic agent is selected from the group consisting of: vinca alkaloids, camptothecins, etoposide, and taxanes.

8. The liposome composition of claim 1, further comprising empty liposomes.

9. A method of delivering a therapeutic agent to a patient, comprising administering to the patient a pharmaceutical composition comprising a liposome-encapsulated therapeutic agent, wherein said liposome comprises phospholipid and cholesterol at a molar ratio from 75/25 (mol/mol) total phospholipid/cholesterol to 25/75 (mol/mol) total phospholipid/cholesterol, wherein at least 50% (molar basis) of total phospholipid present in said liposome is dihydrosphingomyelin (DHSM), and wherein the interior of said liposome comprises $MnSO_4$ or $MgSO_4$.

10. The method of claim 9, wherein the therapeutic agent is an antineoplastic agent.

11. The method of claim 10, wherein the antineoplastic agent is selected from the group consisting of: vinca alkaloids, camptothecins, etoposide, and taxanes.

12. A method of treating a cancer in a mammal, comprising administering to the mammal a pharmaceutical composition comprising a liposome-encapsulated therapeutic agent, wherein said liposome comprises phospholipid and cholesterol at a molar ratio from 75/25 (mol/mol) total phospholipid:cholesterol to 25/75 (mol/mol) total phospholipid:cholesterol, wherein at least 50% of total phospholipids present in said liposome is dihydrosphingomyelin (DHSM), and wherein the interior of said liposome comprises $MnSO_4$ or $MgSO_4$.

13. The method of claim 12, wherein the cancer is a leukemia or lymphoma.

14. The method of claim 12, wherein the cancer is a solid tumor.

15. A method of producing a pharmaceutical composition, comprising loading a liposome comprising phospholipid id and cholesterol at a molar ratio from 75/25 (mol/mol) total phospholipid:cholesterol to 25/75 mol/mol total phospholipid:cholesterol with a therapeutic agent, wherein at least 50% of the total phospholipids present in said liposome is dihydrosphingomyelin (DHSM), and wherein the interior of said liposome comprises $MnSO_4$ or $MgSO_4$.

16. The method of claim 15, wherein said liposome comprises a buffer containing $MnSO_4$ at a concentration equal to or greater than 300 mM, wherein said loading is performed at a temperature equal to or greater than 60° C. and in the presence of an ionophore.

17. A method of loading a therapeutic agent into a liposome comprising: incubating a liposome comprising phospholipid and cholesterol at a molar ratio from 75/25 (mol/mol) total phospholipid:cholesterol to 25/75 (mol/mol) total phospholipid:cholesterol and having an encapsulated medium comprising $MnSO_4$ or $MgSO_4$, wherein at least 50% of the total phospholipid of the liposome is dihydrosphingomyelin (DHSM), with an external solution comprising said therapeutic agent and an ionophore at a temperature greater than 60° C. to form a therapeutic agent-loaded liposome.

18. A kit comprising:
(a) a liposome comprising phospholipid and cholesterol at a molar ratio from 75/25 (mol/mol) total phospholipid:cholesterol to 25/75 (mol/mol) total phospholipid:cholesterol, wherein said at least 50% of total phospholipid present in said liposome is dihydrosphingomyelin (DHSM), and wherein the interior of said liposome comprises $MnSO_4$ or $MgSO_4$, and
(b) a therapeutic agent.

* * * * *

UNITED STATES PATENT AND TRADEMARK OFFICE
CERTIFICATE OF CORRECTION

PATENT NO. : 7,811,602 B2
APPLICATION NO. : 11/131436
DATED : October 12, 2010
INVENTOR(S) : Cullis et al.

Page 1 of 1

It is certified that error appears in the above-identified patent and that said Letters Patent is hereby corrected as shown below:

Column 43, Line 58
"wherein said at least 20% (molar basis) of total" should read, --wherein at least 20% (molar basis) of total--.

Column 44, Lines 48-49
"comprising loading a liposome comprising phospholipid id and cholesterol" should read, --comprising loading a liposome comprising phospholipid and cholesterol--.

Column 44, Lines 50-51
"phospholipid:cholesterol to 25/75 mol/mol total phospholipid:cholesterol" should read, --phospholipid:cholesterol to 25/75 (mol/mol) total phospholipid:cholesterol--.

Column 44, Line 58
"a temperature equal to or greater than 60° C. and in the" should read, --a temperature equal to or greater than 60° C and in the--.

Column 45, Line 2
"C. to form a therapeutic agent-loaded liposome" should read, --C to form a therapeutic agent-loaded liposome--.

Column 46, Line 1
"wherein said at least 50% of total phospholipid" should read, --wherein at least 50% of total phospholipid--.

Signed and Sealed this
Thirty-first Day of May, 2011

David J. Kappos
*Director of the United States Patent and Trademark Office*